United States Patent
Ruiz Lara et al.

(10) Patent No.: US 10,851,382 B2
(45) Date of Patent: Dec. 1, 2020

(54) SYNTHETIC PROMOTOR INDUCED BY ABIOTIC STRESS, GENETIC CONSTRUCT CONTAINING SAME AND PLANT CELLS TRANSFORMED THEREWITH

(71) Applicants: UNIVERSIDAD DE TALCA, Talca (CL); INVERSIONES Y ASESORÍA OLIVARES Y MELOSSI LTDA., Santiago (CL); INVESTIGACIONES AGRÍCOLAS Y FORESTALES DEL MAULE S.A., Talca (CL); FERMELO S.A., Santiago (CL)

(72) Inventors: Simón Aurelio Ruiz Lara, Talca (CL); Enrique Ramón Gonzalez Villanueva, Talca (CL); Jorge Luis Pérez Díaz, Talca (CL); José Ricardo Pérez Díaz, Talca (CL); Mónica Loreto Yañez Chávez, Talca (CL); Isabel Alejandra Verdugo Bastías, Talca (CL); Sebastián Alejandro González Díaz, Talca (CL); Ricardo Javier Chilian, Chillán (CL)

(73) Assignees: UNIVERSIDAD DE TALCA, Talca (CL); INVERSIONES Y ASESORÏA OLIVARES Y MELOSSI LTDA., Santiago (CL); INVESTIGACIONES AGRÍCOLAS Y FORESTALES DEL MAULE S.A., Talca (CL); FERMELO S.A, Santiago (CL)

( * ) Notice: Subject to any disclaimer, the term of this patent is extended or adjusted under 35 U.S.C. 154(b) by 0 days.

(21) Appl. No.: 15/769,527

(22) PCT Filed: Oct. 12, 2016

(86) PCT No.: PCT/CL2016/050053
§ 371 (c)(1),
(2) Date: Apr. 19, 2018

(87) PCT Pub. No.: WO2017/066894
PCT Pub. Date: Apr. 27, 2017

(65) Prior Publication Data
US 2018/0312856 A1 Nov. 1, 2018

(30) Foreign Application Priority Data
Oct. 23, 2015 (CL) .................................. 3143-2015

(51) Int. Cl.
C12N 15/82 (2006.01)
(52) U.S. Cl.
CPC ..... *C12N 15/8216* (2013.01); *C12N 15/8271* (2013.01)

(58) Field of Classification Search
None
See application file for complete search history.

(56) References Cited

U.S. PATENT DOCUMENTS

| 8,471,100 B2 | 6/2013 | Cheng et al. |
| 2013/0291222 A1 | 10/2013 | Cheng et al. |
| 2015/0197768 A1 | 7/2015 | Lopato et al. |

FOREIGN PATENT DOCUMENTS

| CN | 104450708 A | 3/2015 |
| CN | 105602954 A | 5/2016 |
| JP | 2002291473 A | 10/2002 |
| WO | 2008069496 A1 | 6/2008 |
| WO | 2009/060402 A1 | 5/2009 |

OTHER PUBLICATIONS

Tapia et al 2005, Plant Physiol., 138:2075-2086.*
Grandbastien, 2015, Biochimica et Biophysica Acta., 1849:403-416.*
Gilmour, S. et al., "Overexpression of the *Arabidopsis* CBF3 Transcriptional Activator Mimics Multiple Biochemical Changes Associated with Cold Acclimation" Plant Physiology, Dec. 2000, pp. 1854-1865, vol. 124.
Chen, Y. et al., "Overexpression of the regulator of G-protein signalling protein enhances ABA-mediated inhibition of root elongation and drought tolerance in *Arabidopsis*" Journal of Experimental Botany, Feb. 2006, pp. 2101-2110, vol. 57, No. 9.
Pino, M. et al., "Use of a stress inducible promoter to drive ectopic AtCBF expression improves potato freezing tolerance while minimizing negative effects on tuber yield" Plant Biotechnology Journal, 2007, pp. 591-604, vol. 5 Issue 5.
Park, S. et al., "Cold Shock Domain Proteins Affect Seed Germination and Growth of *Arabidopsis thaliana* Under Abiotic Stress Conditions" Plant Cell Physiology, 2009, pp. 869-878, vol. 50 Issue 4.
Shinozaki, K. et al., "Gene networks involved in drought stress response and tolerance", Journal of Experimental Botany, 2007, pp. 221-227, vol. 58, No. 2.

(Continued)

*Primary Examiner* — Jason Deveau Rosen
(74) *Attorney, Agent, or Firm* — Procopio, Cory, Hargreaves & Savitch LLP

(57) ABSTRACT

The present invention relates with the technical field of biotechnology, and particularly provides a promoter inducible under abiotic stress conditions, which is used to regulate expression of a nucleotide sequence encoding a product of interest under these conditions. The invention also refers to a genetic construction containing said promoter, the plant cells transformed with said construction as well as the transgenic plants that can be regenerated from said cells, and which are capable of growing and developing properly, keeping high levels of productive yield under abiotic stress conditions.

16 Claims, 15 Drawing Sheets
Specification includes a Sequence Listing.

(56) References Cited

OTHER PUBLICATIONS

Agarwal, P. et al., "Transcription factors in plants and ABA dependent and independent abiotic stress signalling" Biologia Plantarum, 2010, pp. 201-212, vol. 54, Issue 2.

Pauls, P. et al., "Expression of the tobacco Tnt1 retrotransposon promoter in heterologous species" Plant Molecular Biology (1994) pp. 393-402, vol. 26.

Tapia, G. et al., "Involvement of Ethylene in Stress-Induced Expression of the TLC1.1 Retrotransposon from Lycopersicon chilense Dun" Plant Physiology, (Aug. 2005), pp. 2075-2086, vol. 138.

Sambrook, J. et al., "Molecular Cloning a Laboratory Manual" 1989, Cold Spring Harbor Laboratory Press, United States of America.

Wi, S. et al., "Overexpression of carnation S-adenosylmethionine decarboxylase gene generates a broad-spectrum tolerance to abiotic stresses in transgenic tobacco plants" Plant Cell Rep (2006) pp. 1111-1121, vol. 25.

Morosinotto, T. et al., "Mutation Analysis of Lhca1 Antenna Complex" The Journal of Biological Chemistry (Sep. 27, 2002), pp. 36253-36261, vol. 277, No. 39.

Salazar, M. et al., "The promoter of the TLC1.1 retrotransposon from Solanum chilense is activated by multiple stress-related signaling molecules" Plant Cell Rep (2007), pp. 1861-1868, vol. 26.

Lescot, M. et al., "PlantCARE, a database of plant cis-acting regulatory elements and a portal to tools for in silico analysis of promoter sequences" Nucleic Acids Research (2002), pp. 325-327, vol. 30, No. 1.

Higo, K. et al., "Plant cis-acting regulatory DNA elements (PLACE) database: 1999" Nucleic Acids Research (1999) pp. 297-300, vol. 27, No. 1.

Liang, P. et al., "Differential Display of Eukaryotic Messenger RNA by Means of the Polymerase Chain Reaction" Science Magazine (Aug. 14, 2002), pp. 967-971, vol. 257.

Blast [online] National Center for Biotechnology Information [retrieved Apr. 18, 2018]. Retrieved from the internet: <URL:https://blast.ncbi.nlm.nih.gov/Blast.cgi >.

International Search Report for related PCT Application No. PCT/CL2016/050053, dated Mar. 17, 2017, 6 pages; English translation provided.

\* cited by examiner

SEQ. ID. N°1

```
TGAGGAGTCC ATCCGCGAGA ACCAAACTTT GAATAACTTT GTGCCACTGC AGAAGTTTGG    60
TAGAGTTGGT AATCTATGAA GAAGAAAAAT TTGTTTTGTG CCATCTAGAA GCTTTGGTAG   120
AGTAGGTGAG CTATGAAGAA GAAAAAATTG TTTTGTGCCA CTGCAGAAGT TTGGTAGAGT   180
TGGTAATCTA TGAAGAAGAA AAATTTGTTT TGTGCCATCT AGAAGTTTG GTAGAGTAGG   240
TGAGCTATGA AGAAGAAAAA ATTGTTTTTC TTCTATAGCA CATTGGAGG GTAGTGTATT   300
TGTTCTCTAT AAAAGGGAGG ACAATTCTTC ATTCTAAGTA CACCAAAAAG AATTACAAAG   360
GAGAGAAAAA AAGAGTGAGG CATC                                          384
```

FIGURE 1

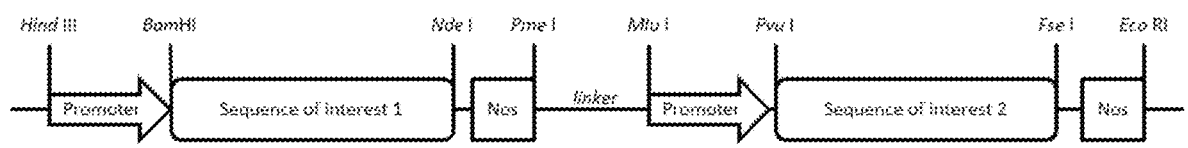

FIGURE 2

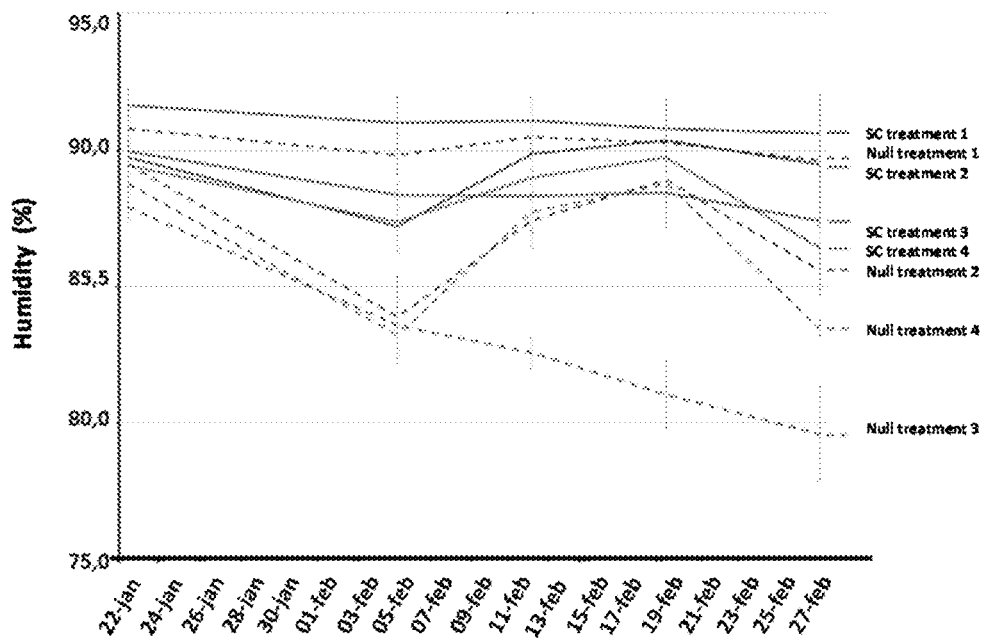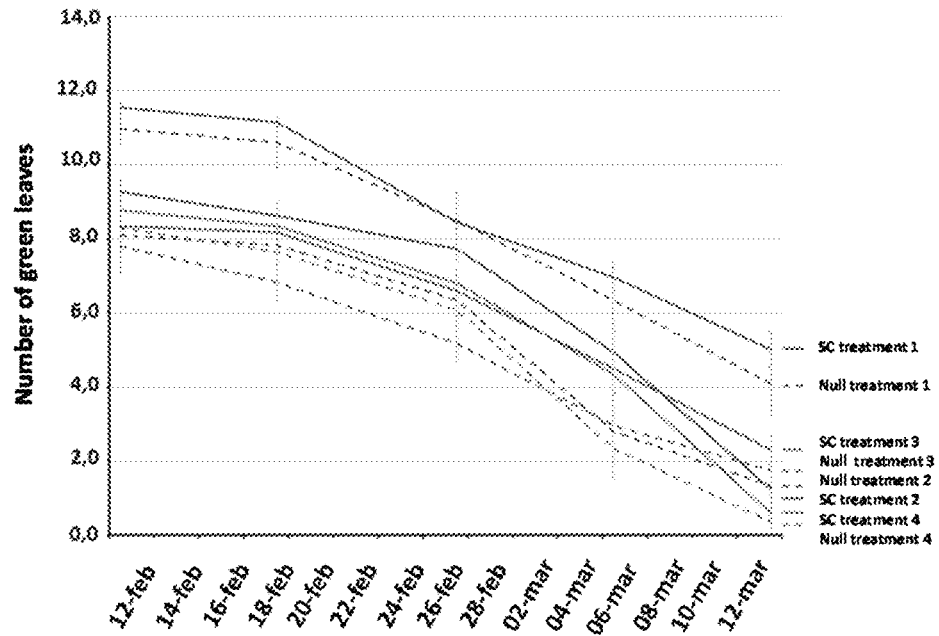
FIGURE 11

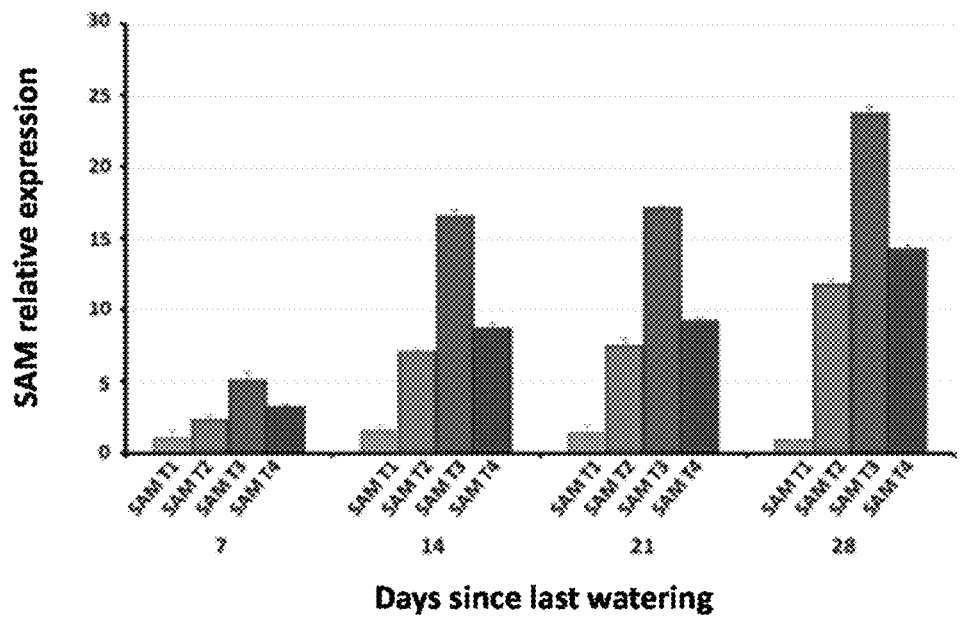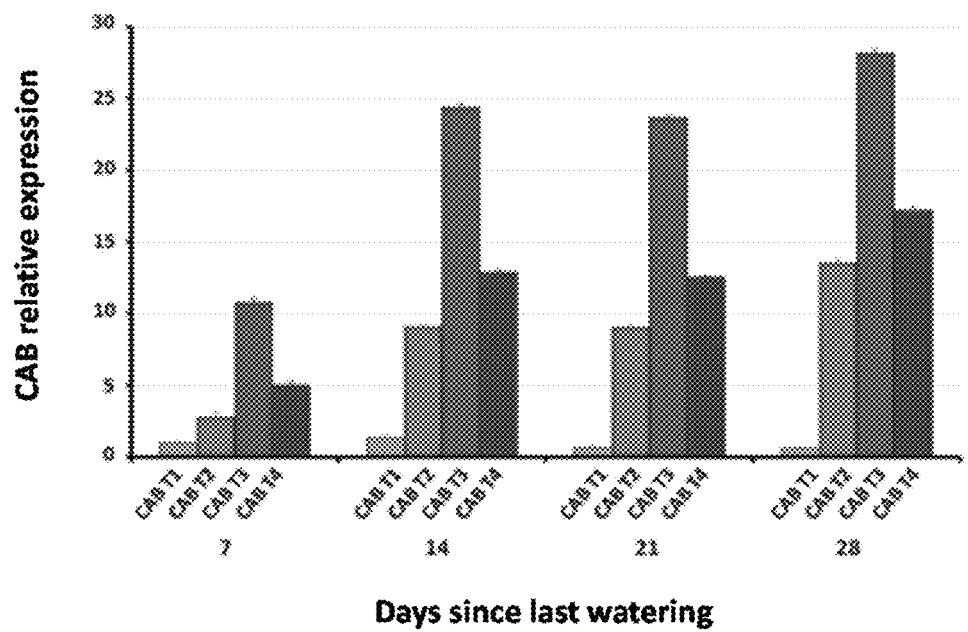
FIGURE 12

Corn cobs with continous watering
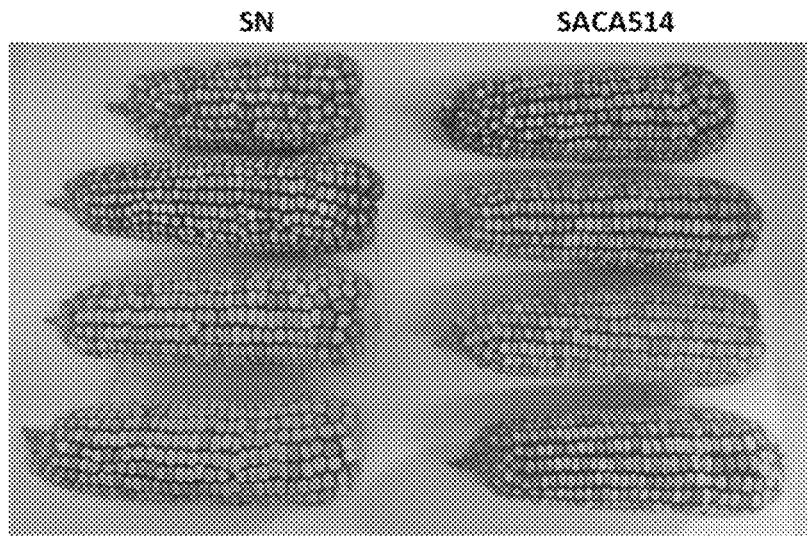
Corn cobs with very severe drought
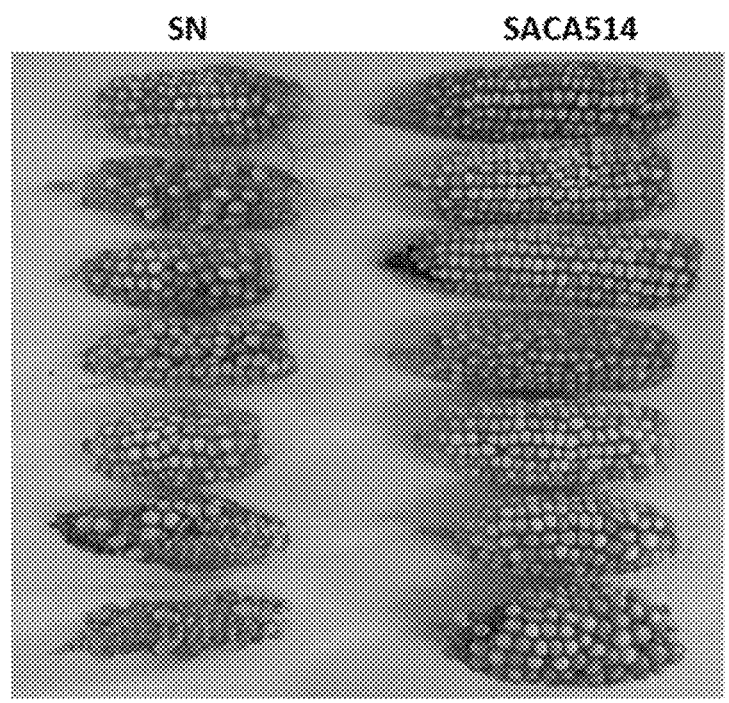
FIGURE 18

SYNTHETIC PROMOTOR INDUCED BY ABIOTIC STRESS, GENETIC CONSTRUCT CONTAINING SAME AND PLANT CELLS TRANSFORMED THEREWITH

CROSS-REFERENCE TO RELATED APPLICATIONS

This application is a U.S. National Stage entry of PCT Application No: PCT/CL2016/050053 filed Oct. 12, 2016, which claims priority to Chilean Patent Application No. 3143-2015, filed Oct. 23, 2015, the contents of which are incorporated herein by reference.

TECHNICAL FIELD

The present invention relates with the technical field of biotechnology. More particularly, the present invention provides an abiotic stress-induced promoter which is used for expression regulation of a nucleotide sequence encoding a product of interest under these conditions. The invention also refers to a genetic construct containing said promoter, plant cells transformed with said construct, and the transgenic plant that can be regenerated from said transformed plant cells, which is capable of growing and developing properly under abiotic stress conditions.

BACKGROUND OF THE INVENTION

The extreme climate changes occurring at the present time significantly affect agricultural crops, subjecting plants to abiotic stress conditions such as extreme temperatures, excess of salt in soils and water deficiency, among other adverse conditions, which all together cause production decrease and important economic losses in this industrial sector.

Therefore, it is crucial to obtain agricultural crops that are more resistant or tolerant to these extreme environmental factors. Usually this can be performed through conventional improvement of crops, namely, using artificial selection or selective plant breeding, thus obtaining varieties better adapted to environment conditions. However, this process is highly laborious and not always efficient due to the need of successive repetition steps of selecting and discarding varieties, and consequently it depends on each particular plant species and its cultivation cycle.

A more efficient technique for crop improvement is achieved by transferring of coding DNA sequences, which confer the plant a greater tolerance to environmental harsh conditions. The advantages of this technique are based on the possibility of transferring any genetic element and, therefore, it is possible to generate crops with diverse attributes. To do so, it is of great importance the expression regulation of the coding DNA sequence of interest through a regulatory DNA sequence or promoter, which can determine when, where and how intense the coding sequence will be transcribed in the plant. This regulation is highly specific and precise, since genetic modification of plants with inadequate promoters frequently produces plants with undesired phenotypic characteristics. For example, when the gene of interest is regulated under the control of a constitutive promoter such as the promoter of Cauliflower mosaic virus (CaMV35S) it is possible to obtain plants with a diminished growth and development (dwarf plants); plants with low chlorophyll production levels (chlorosis) that even show necrosis in their tissues (Gilmour et al., 2000, *Plant Physiol* 124(4): 1854-1865; Chen et al, 2006, *J Exp Bot* 57(9): 2101-2110; Pino et al, 2007, *Plant Biotechnol J* 5(5): 591-604; Park et al, 2009, *Plant Cell Physiol* 50(4): 869-878).

An alternative to overcome these problems is the utilization of specific promoters capable of controlling expression of a coding DNA sequence in a determined developmental stage, in a specific plant tissue, or only in the presence of a particular stimulus. Said stimuli, such as drought stress and salinity, can trigger a plant response modulated by the presence of the hormone abscisic acid (ABA) and/or through a pathway independent from this plant hormone (Shinozaki and Yamaguchi-Shinozaki, 2007, *J Exp Bot* 58: 221-7). The ABA-dependent regulatory system involves transcription factors with binding sites for ABA response elements (also known as ABREs) denominated AREBs/ABFs and others termed MYC/MYB. Other transcription factors are involved in ABA-independent pathways that are responsive to dehydration, such as DREB/CBF (Agarwal and Jha, 2010, *Biol Plant* 54(2): 201-212), among others.

In the prior art it is possible to find diverse strategies to obtain promoters inducible by abiotic stress in plants which respond to some previously mentioned transcription factors. For example, document WO2008069496 describes plants transformed with a vector containing a promoter inducible by abiotic stress, which is operably linked to a gene encoding the enzyme zeaxanthin epoxidase. Preferably, said promoters are derived from *Arabidopsis thaliana*, such as promoters RD29A, Rab18, COR15A, RD22, LOSS, among others mentioned. These promoters are preferably induced by osmotic stress, high salinity or drought, and have binding sites for ABA-dependent and independent transcription factors. On the other hand, patent document U.S. Pat. No. 8,471,100 discloses a nucleotide sequence originated from poplar, having a regulatory activity induced by stress and capable of activating transcription when the plant is subjected to extreme temperature conditions, drought, highly saline soils, among other factors. On the other hand, document US 2015/0197768 describes promoter Cor410b inducible by cold stress, drought and physical stress, which was isolated from a gene present in wheat encoding a protein denominated dehydrin that is produced under said stimuli.

Another particular type of stress-induced promoters outlined in literature are those derived from retrotransposons. It is believed that regulatory regions from active transposons constitute the plant defense system against adverse conditions. Due to this, various researchers have used these promoters with the aim of expressing heterologous genes in plants with a view to improve their tolerance to abiotic stress. This is the case of the promoter of retrotransposon Tnt1 from *Nicotiana tabacum*, which is capable of activating transcription of a heterologous gene in *Brassica napus* plants (Pauls et al., 1994, *Plant Mol Biol* 26: 393-402). With the same purpose, retrotransposon-derived promoters have also been isolated from oat as described in document JP2002291473, or promoter PCb-RARE originated from *Carallia brachiata* as described in document CN104450708.

Particularly, retrotransposon TLC1.1 also has a promoter region inducible by abiotic stress, which comprises response regions to stress signals, including ethylene, methyl jasmonate, salicylic acid, among others (Tapia et al., 2005. *Plant Physiol* 138: 2075-2086). However, many developmental stages in the plant are regulated by ethylene and when that compound is present, the promoter could be induced in undesired moments, therefore producing deleterious effects to the plant. Based upon the foregoing, there exists a deficiency in the state of the art regarding to promoters originated from genetically modified retrotransposons which demonstrate an improved precision in the regulation of effector genes and only respond specifically in presence of transcription factors of interest, so that regulated genes express conveniently in particular stress conditions and not in other stages that could interfere with the adequate development of the plant.

SUMMARY OF THE INVENTION

The present invention refers to a promoter inducible by environmental conditions such as abiotic stress, selected from the group consisting of:
  a nucleotide sequence comprising the nucleotide sequence shown in SEQ ID NO:1;
  any fragment from the nucleotide sequence SEQ ID NO:1 which maintain the capacity to regulate gene expression under abiotic stress conditions; and
  a nucleotide sequence sharing at least 80% of identity with sequences a) or b).

Another object of the present invention is a DNA construct comprising the promoter previously described operably linked to a DNA sequence encoding a product of interest. Said DNA sequence encoding the product of interest is preferably selected from:
  a nucleotide sequence comprising the nucleotide sequence shown in SEQ ID NO:2 or a fragment thereof;
  a nucleotide sequence comprising the nucleotide sequence shown in SEQ ID NO:3 or a fragment thereof;
  a nucleotide sequence sharing at least 80% of identity with either nucleotide sequence in SEQ ID NO:2 or SEQ ID NO:3; and
  any combination of the sequences previously mentioned.

In a preferred embodiment of the invention, each promoter present in DNA construct is operably linked to each one of the DNA sequences encoding the product or products of interest in said construct. Additionally, each sequence with its respective promoter is separated from each other by linker sequences, which preferably correspond to random nucleotide sequences of 120 to 400 base pairs in length.

In another preferred embodiment, DNA sequences shown in SEQ ID NO:2 and SEQ ID NO:3 encode products of interest corresponding to the enzyme S-adenosylmethionine decarboxylase and protein 1 (CAB6), chlorophyll a/b binding protein in the light harvesting complex from photosystem I (PSI), respectively. Preferably, such DNA sequences originate from genus *Solanum*, particularly from *Solanum chilense* (syn. *Lycopersicon chilense*).

Other object of the present invention is an expression vector comprising the promoter or the DNA construct previously mentioned.

An additional object of the present invention is a transformed cell comprising the promoter, or the DNA construct, or the recombinant vector previously described.

Another object of the present invention is a transgenic cell comprising inserted in its genome the promoter, or the DNA construct, or the recombinant vector previously described.

Other additional objects of the present invention are a callus of cells obtained by culturing the transgenic cells of the present invention; as well as the transgenic plant obtained by regeneration of said transgenic callus, expressing one or more DNA sequences encoding products of interest which finally confer tolerance against abiotic stress to the plant, without interfering with its development.

The present invention also refers to the method for expressing a nucleotide sequence encoding a product of interest under abiotic stress conditions, consisting in transforming a cell from a plant with the expression vector of the present invention; obtaining from said cell a transgenic callus and regenerating a plant from said callus. Preferably, said plant is selected from the group consisting in monocotyledons and dicotyledons.

BRIEF DESCRIPTION OF THE DRAWINGS

FIG. 1 shows PTS514 promoter according to one of its preferred embodiments.

FIG. 2 shows a diagram of SACA514 construct according to one of its preferred embodiments.

FIG. 11 shows graphs referring to the relative content of water and senescence level (stay-green) of transgenic Hi II×B73 maize plants containing SACA514 construct in comparison with null segregant plants, under different treatments of drought.

FIG. 12 shows graphs with the results of total RNA expression of nucleotide sequences disclosed in SEQ ID NO:2 (SAM, FIG. 12A) and SEQ ID NO:3 (CAB, FIG. 12B) under different drought treatments.

FIG. 18 shows images of corns derived from transgenic Hi II×B73 maize plants containing SACA514 construct in comparison with null segregant plants, under continuous watering treatment (normal) and severe drought treatment.

DETAILED DESCRIPTION OF THE INVENTION

Figure 3:
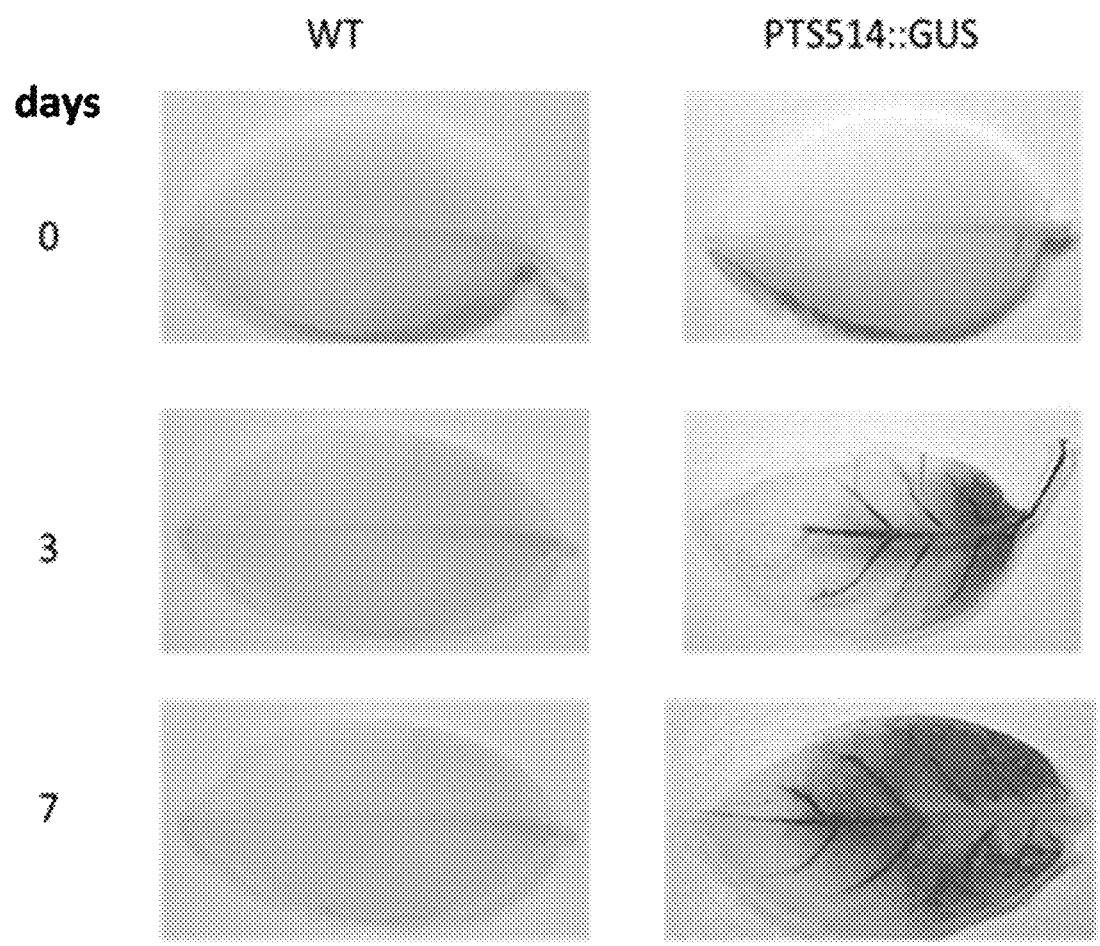
FIG. 3 is an image of a histochemical analysis of wild-type tobacco leaves and leaves from tobacco plants transformed with PTS514 promoter operably linked to a DNA sequence encoding enzyme β-glucuronidase.

As described, the present invention refers to a promoter which is inducible under abiotic stress conditions and regulates expression of DNA sequences encoding a product of interest in a plant, a DNA construct comprising said promoter operably linked to each DNA sequences encoding a product of interest, an expression vector comprising said promoter or the DNA construct previously mentioned, a transformed cell, a transgenic cell, a callus of transgenic cells originated from the culture of said transgenic cells; and a transgenic plant obtained by regeneration of said transgenic callus, containing the promoter, or the DNA construct or the expression vector previously mentioned, conferring to the plant the required tolerance for adequately surviving and developing against abiotic stress conditions.

All technical and scientific terms used to describe the present invention have the same meaning understood by a person having a basic knowledge in this technical field. Notwithstanding, to define the scope of the invention more clearly, a list of terminology used in this description is included down below.

It should be understood that as used herein, the term "promoter" refers to a nucleotide sequence which regulates the beginning of transcription, and comprises a TATA box involved in the recognition and binding of RNA polymerase II and other proteins needed to start transcription process. Said needed proteins correspond to transcription factors that bind to specific sequence regions in the promoter.

It is to be understood that the term "abiotic stress" refers to every alteration produced by non-biological environmental factors, which originates a negative effect in plant physiology and development. Among these factors, the excess or lack of light or water, extreme temperatures, high concentrations of ions and salts and atmospheric contaminants are found, among others.

It is to be understood that the term "nucleotide sequence" refers to a double strand of DNA, or a single strand of DNA, either natural or synthetic, or products derived from transcription of said DNA sequence (for example, RNA molecules). At the same time, "DNA sequence encoding a product of interest" should be understood as a nucleotide sequence able to be transcribed into a molecule of functional RNA, or as a sequence encoding a functional peptide or protein of interest for the present invention. It should be understood that the present invention is not related to genomic nucleotide sequences in its natural state, but to nucleotide sequences in an isolated, purified, partially purified or recombinant state obtained through any method of genetic engineering known in the state of the art.

The term "transgene" should be understood as any nucleotide sequence or genetic material which is transferred naturally or by means of genetic engineering techniques from an organism to another. Those foreign, artificial or synthetic nucleotide sequences that are transferred to an organism are also considered transgenes.

It should be understood that as used herein, the term "identity" regarded as nucleotide sequences refers to the percentage of identical nucleotides shared by the sequences being compared with respect to each other, over a comparison window. The percent of identity can be calculated by using an algorithm of sequence comparison or by means of manual alignment and visual inspection. For example, the sequences and percentages of identity can be obtained using computing resources available on Internet such as BLAST tool or the program FastDB. Sequence identity can also be determined through hybridization assays of the same. The higher the degrees of stringency used in the hybridization assay, the greater is the sequence complementarity required for these to hybridize. The high stringency conditions are described by Sambrook et al. (Molecular Cloning A Laboratory Manual, Cold Spring Harbor Press, 1989).

It is to be understood that the term "DNA construct" refers to a nucleotide sequence created artificially through genetic engineering techniques, which generally comprises a transcription promoter sequence operably linked to a DNA sequence encoding a product of interest and, adjacent to the same, a DNA sequence for transcription termination. This DNA construct, in order to be expressed in a proper host such as a prokaryotic cell, a eukaryotic cell or a higher organism, must be inserted in an expression vector, which contains all DNA sequences needed for its adequate expression in said host, together with a number of molecular markers allowing detection and selection of those hosts that have been transformed.

The term "linker sequence" should be understood as a nucleotide sequence created artificially through genetic engineering tools, which allows to create an adequate spacing between the transcription terminator of a DNA sequence encoding a protein of interest and the following promoter of a DNA sequence encoding a second protein of interest. This linker sequence corresponds to a non-coding nucleotide sequence randomly selected, and it can be used as much as needed in the DNA construct to separate DNA sequences encoding proteins of interest.

It should be understood that as used herein, the term "transformed cell" relates to a host cell that can be a prokaryotic or eukaryotic, to which an exogenous DNA sequence is incorporated. Similarly, the term "transgenic cell" should be understood as a prokaryotic or eukaryotic cell to which an exogenous DNA sequence is incorporated, but this sequence is inserted in the genome of said cell.

It is to be understood that the term "transgenic callus" refers to a culture of transgenic plant cells that have formed a mass of undifferentiated cells. The term "transgenic plant" should be understood as a plant regenerated from a transgenic callus.

As described, an object of the present invention refers to a promoter comprising a nucleotide sequence of synthetic origin, shown in SEQ ID NO:1. The scope of the present invention includes any fragment of said nucleotide sequence SEQ ID NO:1 maintaining the capacity to regulate gene expression under abiotic stress conditions, or a nucleotide sequence sharing at least 80% of identity with the nucleotide sequence previously mentioned. Said abiotic stress conditions preferably refer to stress caused by water deficiency, however, it must be understood for the scope of the present invention that said promoter can also respond to other types of physical stress (such as cuts, tears, etc.), thermal stress (extremely high temperatures over 45° C., or extremely low temperatures under 5° C.), stress by salt excess, and any other type of abiotic stress known by a person having basic knowledge in the technical field.

FIG. 1 shows a preferred embodiment of the promoter of the present invention, termed PTS514. This promoter has a preferential length of 384 base pairs and contains a nucleotide sequence of 57 base pairs repeated in tandem (SRT1, SRT2, SRT3, SRT4), which contains specific regions for the recognition of transcription factors associated with the response against abiotic stress. This promoter has putative MYB transcription factor binding sites (AACCAAA) at position 20-26, four tissue-specific GCN4 binding domains (TGTGCC) at positions 40-46, 97-102, 154-160 and 211-217; five putative binding sites (AAGAAGAAA) for GT-1 and TCA transcription factors at positions 79-91, 136-148, 193-205, 250-262 and 360-372. PTS514 promoter of the present invention offers the advantage of not inducing transcription in response to ethylene molecules, chemical compound present in multiple developmental stages of the plant. Therefore, the promoter of the present invention is induced only by the plant response under abiotic stress conditions, without affecting its normal development.

In a preferred embodiment, the promoter of the present invention is flanked at the 5' and 3' ends, respectively, by nucleotide sequences recognized by Hind III and Bam HI restriction enzymes, to facilitate cloning in a vector of interest. It is worth noting that said sequences to be recognized by restriction enzymes can be modified for any other sequence to be recognized by adequate restriction enzymes, that is to say, not interfering with the rest of the DNA construct or the vector of interest in which the gene of interest is being cloned; and those mentioned are only a preference that does not affect functionality or the scope of the present invention.

Other object of the present invention refers to a DNA construct comprising the promoter previously described, operably linked to a DNA sequence encoding a product of interest.

In a preferred embodiment, the DNA sequence or the gene encoding the product of interest is selected from the group consisting in a nucleotide sequence shown in SEQ ID NO:2 or a fragment thereof, or a nucleotide sequence shown in SEQ ID NO:3 or a fragment thereof, or a nucleotide sequence sharing at least 80% of identity with any of the nucleotide sequences already mentioned, or any combination of said nucleotide sequences.

The DNA construct of the present invention may comprise any of the sequences previously mentioned or any other encoding a product of interest, at any combination, and with any promoter suitable for expression of said product of interest under abiotic stress conditions. In a preferred embodiment, the DNA construct of the present invention comprises the PTS514 promoter operably linked to each of the DNA sequences encoding a product of interest in said construct; and at the same time, said DNA sequences at the 3' end have a linked transcription terminator, preferably NOS terminator.

FIG. 2 shows a diagram of a preferred embodiment of said DNA construct, termed SACA514. The sequence of said DNA construct is shown in SEQ ID NO:4. Particularly, SACA514 construct comprises two DNA sequences, each one encoding different products of interest.

Additionally, in a preferred embodiment of the present invention, SACA514 construct comprises a linker sequence (SEQ ID NO:5) between the transcription terminator of a nucleotide sequence encoding a product of interest and the promoter of the following nucleotide sequence encoding a second product of interest. Said linker sequence preferably comprises a nucleotide sequence selected randomly, which is not recognizable by restriction enzymes and does not encode a product. In a preferred embodiment, said linker sequence has 203 base pairs in length.

Said products of interest encoded by sequences SEQ ID NO:2 and SEQ ID NO:3, corresponding to a preferred embodiment of the present invention, encode the enzyme S-adenosylmethionine decarboxylase and the protein 1 (CAB6), chlorophyll a/b binding protein in the light harvesting complex from photosystem I (PSI), respectively. Enzyme S-adenosylmethionine decarboxylase participates in the metabolic pathway of polyamines producing decarboxylated S-adenosylmethionine. This substrate together with the compound putrescine, allow the enzyme spermidine synthase to form spermidine. Overexpression of this coding sequence allows transgenic plants containing it to increase its tolerance to different types of abiotic stress (Wi et al., 2006, *Plant Cell Rep* 25(10): 1111-21). On the other hand, when plants are exposed to conditions causing photo oxidative damage, CAB6 protein belonging to LCH superfamily (Light-harvesting chlorophyll a/b-binding proteins) takes a conformation capable of dissipating the excess of excitation energy as heat, then performing a photo-protective function (Morosinotto et al., 2002, *J Biol Chem* 277(39): 36253-61). Both proteins develop a protective role in the plant independently from each other, when abiotic stress conditions are present.

In a preferred embodiment, sequences encoding said products of interest are isolated and purified from plants of the genus *Solanum*, particularly from *Solanum* chilense (syn. *Lycopersicon chilense*). However, the present invention is not limited to these species of origin, because there exist various alternatives of plants containing nucleotide sequences encoding the mentioned proteins that can be used indifferently. Additionally, the purified and isolated nucleotide sequences are modified to avoid the presence of sequences recognizable by restriction enzymes, without modifying the implicated codons.

Another object of the present invention is an expression vector comprising the promoter and/or the DNA construct previously described.

In the context of the present description, the term "expression vector" should be understood as any means for transferring nucleotide sequences or foreign genes in a host cell, being prokaryote or eukaryote, for example: plasmid vectors, cloning vectors, binary vectors and viral vectors, among others, without limitation to said examples.

Another object of the present invention is a transformed cell comprising the promoter, or the DNA construct, or the expression vector previously described. Said transformed cell can be prokaryote or eukaryote.

Another object of the present invention is a transgenic cell comprising the promoter, or the DNA construct, or the expression vector previously described. Said transgenic cell can be prokaryote or eukaryote, or it can also refer to a protoplast. The term "transgenic" should be understood as an integration of a nucleotide sequence in the genome of said cell, which can be inherited by its progeny.

Other objects of the present invention are a transgenic callus corresponding to the culture of the transgenic cells previously mentioned, and a transgenic plant regenerated from said callus comprising the promoter, or the DNA construct, or the expression vector previously described. It is to be understood that the scope of the present invention seeks to include any part of the transgenic plant such as tissues, flowers, stems, fruits, seeds, leaves or roots. Said transgenic plant can be monocotyledon or dicotyledon.

An additional object of the present invention is a method for expressing a nucleotide sequence encoding a product of interest in a plant under abiotic stress conditions, comprising the steps of transforming a plant cell with the expression vector that includes the promoter of the present invention, with the subsequent insertion of said vector in the genome of said plant cell; obtaining from that transgenic cell a transgenic callus; and regenerating a plant from said callus to finally obtain a transgenic plant. The transformation methods to insert DNA sequences in plant cells may be any of the appropriate methods for the introduction of said genetic material in the host, such as electroporation, *Agrobacterium* mediated transformation, biolistics, or direct genetic transfer, without limiting to these examples.

In a preferred embodiment of the present invention, the cell, the callus and the transgenic plant are selected from the group consisting in, but not limited to, maize (*Zea mays*), tomato (*Solanum lycopersicum*), potatoes (*Solanum tuberosum*), rice (*Oryza sativa, Oryza glaberrima*), rye (*Secale cereale*), wheat (*Triticum* spp) sunflower (*Helianthus* spp.), soy (*Glycine max*), tobacco (*Nicotiana tabacum*), coffee (*Cofea* spp.), tea (*Camellia sinensis*), cotton (*Gossypium* spp.), cocoa (*Theobroma cacao*), avocado (*Persea americana*), olive (*Olea europea*), citrus trees (*Citrus* spp.), and any other vegetable, ornamental plant, trees and conifers.

The following examples are intended to illustrate the invention and its preferred embodiments, but they should not be considered under any circumstances to restrict the scope of the invention, which is determined by the content of the claims attached hereto.

EXAMPLES

Example 1: Synthesis of PTS514 Promoter

The basis of PTS514 promoter of the present invention originates from the U3 sequence of the 5' LTR region of the TLC1.1 retrotransposon from *Solanum chilense* (Tapia et al., 2005, *Plant Physiol* 138: 2075-86) and the promoter sequence derived from the former, named PTRS1*/2* (Salazar et al., 2007, *Plant Cell Report* 26: 1861-68). Both promoter sequences contain a sequence repeated in tandem of 57 base pairs in length, within which exist transcription factors response elements activated by different signal transduction pathways. One of those elements is a nucleotide sequence responsive element which responds to ethylene induced transcription and it is not present in PTRS1*/2* promoter, because it has been replaced by nucleotide sequences recognizable by restriction enzymes Pst I and Xba I, as shown in black in FIG. 1. For PTS514 promoter synthesis, two new tandem sequences of 57 base pairs in length were added to PTRS1*/2* promoter starting from nucleotide 37, which are indicated as SRT1, SRT2, SRT3 and SRT4 in FIG. 1; therefore obtaining a sequence of 384 base pairs in length. Additionally, restriction enzyme recognition sequences for Hind III and Bam HI were added at the 5' and 3' ends. The PTS514 promoter sequence was sent to the company Integrates DNA Technologies (IDT) in USA for its automated synthesis.

Once synthesized, PTS514 promoter sequence was cloned into pUC57 vector using restriction enzyme recognition sequences for Hind III and Bam HI. The plasmid having PTS514 promoter was amplified in *E. coli* DH5-α. The recombinant plasmids obtained were sent to Macrogen Inc. (Chongro-ku, Seoul, Korea) for sequence analysis service with the purpose of confirming its nucleotide sequence.

Putative transcription factor binding sites existing in PTS514 promoter were obtained by using data bases useful for searching regulatory sequences in promoters of plant genes, such as PlantCARE (Lescot et al., 2002, *Nuc Acid Res* 30(1): 325-327), PLACE (Higo et al., 1999, *Nuc Acid Res* 27(1): 297-300) and AGRIS (Davuluri et al., 2003, *BMC Bioinfor* 4(1): 25). As mentioned before, this promoter has putative MYB transcription factor binding sites (AAC-CAAA) at position 20-26, four tissue-specific GCN4 binding domains (TGTGCC) at positions 40-46, 97-102, 154-160 and 211-217; five putative binding sites (AAGAAGAAA) for GT-1 and TCA transcription factors at positions 79-91, 136-148, 193-205, 250-262 and 360-372. FIG. 1 also shows a putative TATA box, delineated in a black rectangle.

Example 2: Functional Analysis of Promoter Sequence PTS514

Stable transformation of tobacco plants were performed, with pBI121 binary vector containing PTS514 promoter construct operably linked to the nucleotide sequence encoding protein β-glucuronidase. Said transgenic plants were subjected to stress by water deficiency and some leaves of the same were collected 0, 3 and 7 days from the moment of watering suspension. Collected leaves were subjected to histochemical assay. Results of this experiment are shown in FIG. 3, where WT represents leaves from wild type plants and PTS514::GUS correspond to leaves of transgenic plants comprising promoter PTS514. Results reveal that said promoter shows a basal promoter activity, which is highly increased when transgenic plants are exposed to abiotic stress conditions, therefore indicating that the promoter is induced under these conditions.

Example 3: Obtention of SchSAMdc and SchLhca1 Sequences

Nucleotide sequences SchSAMdc and SchLhca1 were detected, isolated and purified according to the differential display method, following the protocol described by Liang and Pardee (1992), starting from leaves of *Solanum chilense* plants exposed to drought and cold stress, respectively. Complementary DNA (cDNA) sequences obtained were cloned into pGEM-T Easy System I vector (Promega) and the resulting plasmid was amplified in *E. coli* DH5-α. The obtained plasmids containing cDNA were sequenced using T7Sequencing™ Kit (Amersham Pharmacia Biotech). Analysis of deduced nucleotide and amino acid sequences was performed using BLAST advanced programs, which made possible the assignment of names and putative functions by sequence homology.

Figure 4:
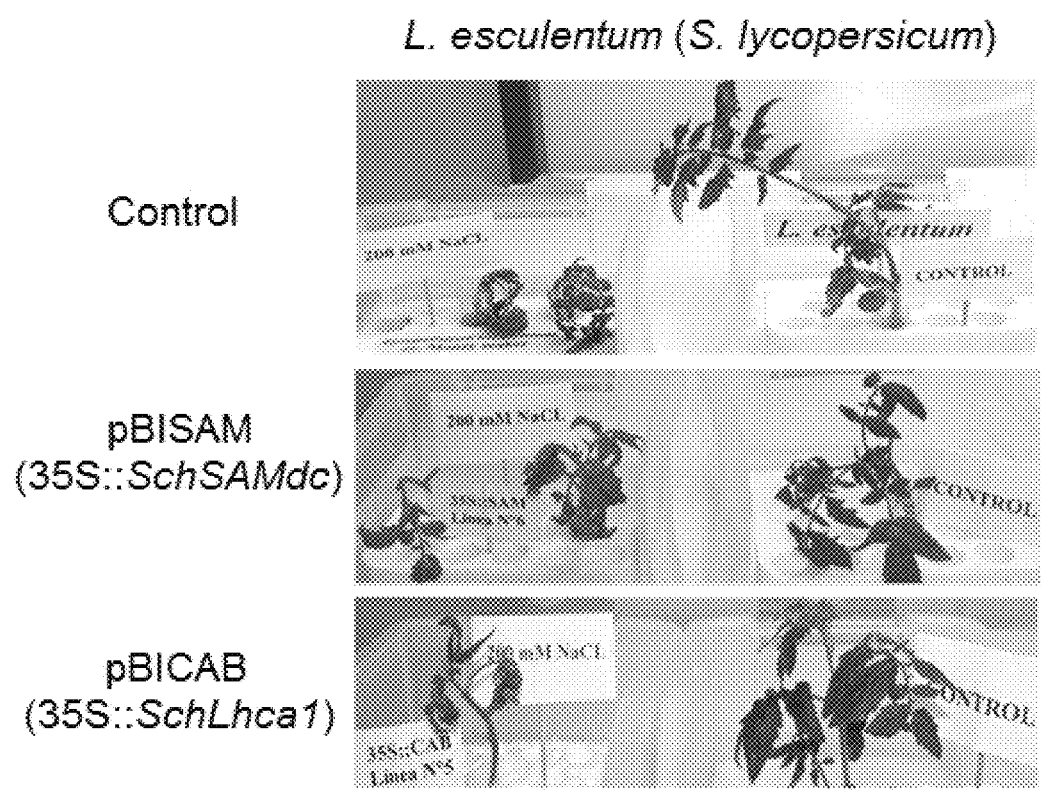
FIG. 4 shows images of *Solanum lycopersicum* wild type plants and transgenic plants from the same species, expressing SchSAMdc and SchLhca1 nucleotide sequences under the 35SCaMV constitutive promoter, in conditions of high salinity.

Example 4: Expression of SchSAMdc and SchLhca1 Induced by 35SCaMV Promoter in Tomato Plants Nucleotide sequences SchSAMdc and SchLhca1 previously obtained were amplified by PCR using adequate primers, to add restriction enzyme recognition sequences for Bam HI and Sst I at 5' and 3' ends. In that way, SchSAMdc and SchLhca1 were cloned into pBI121 binary vector, replacing the nucleotide sequence encoding protein β-glucuronidase. Therefore, said sequences remained under the control of promoter 35S from Cauliflower Mosaic Virus (CaMV) contained in said vector. These recombinant vectors were termed pBISAM and pBICAB, respectively, and were used to transform tomato plants *Solanum lycopersicum* through *Agrobacterium tumefaciens*. FIG. 4 shows pictures of the results obtained with wild type *L. esculentum* (*S. lycopersicum*), var. MoneyMaker plants as control, which were subjected to 10 days of hydroponic cultivation in normal conditions or in high salinity (200 nM NaCl); and transgenic plants transformed with pBISAM (35S::SchSAMdc) vector, or pBICAB (35S::SchLhca1) vector, which were subjected to the same 10 days of hydroponic cultivation in normal conditions or in high salinity (200 nM NaCl). As can be noted, transgenic plants constitutively overexpressing SchSAMdc or SchLhca1 show an increase in abiotic stress tolerance.

Figure 5:
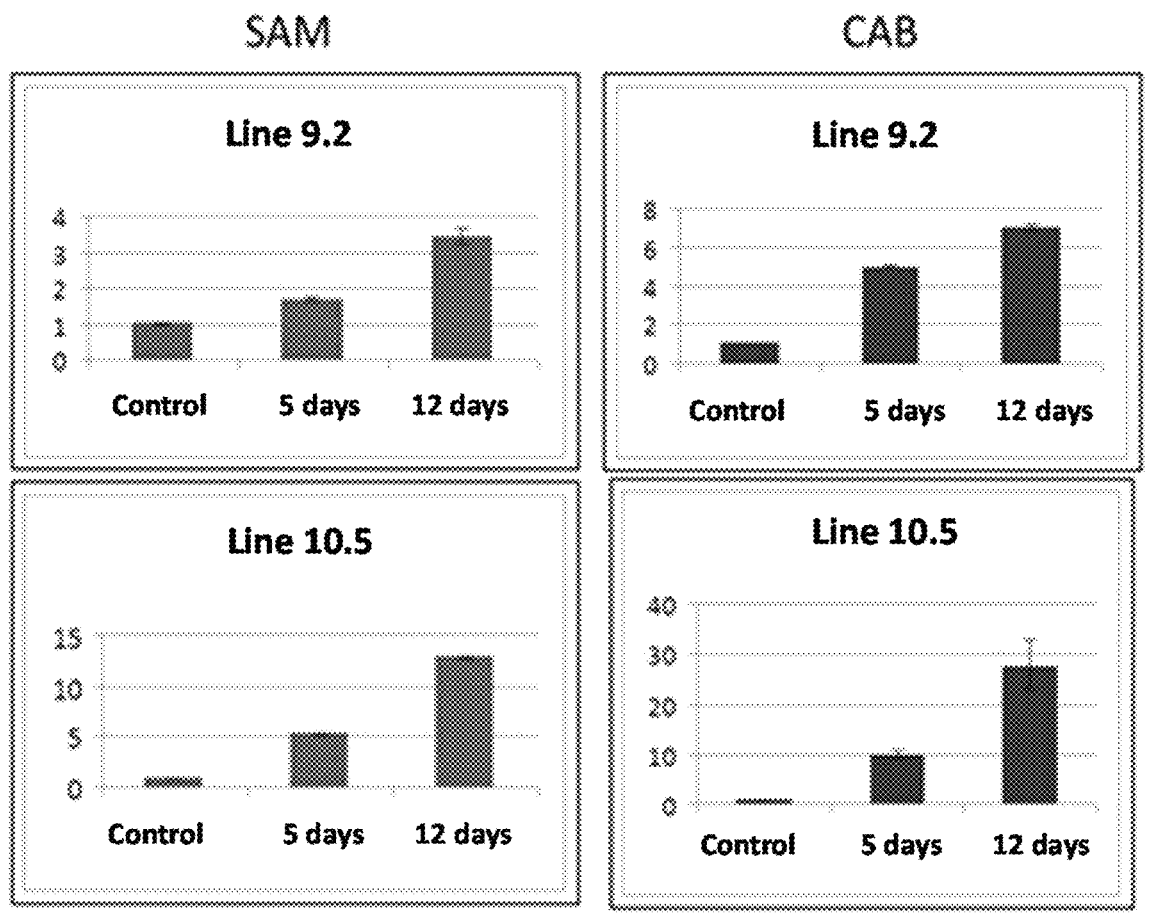
FIG. 5 shows graphs indicating total RNA amount expressed in different lines of Hi ll maize transgenic plants transformed with pTFSAM514 or pTFCAB514 vectors and subjected to watering suspension.

Example 5: Expression of SchSAMdc and SchLhca1 Induced by Promoter PTS514 in Maize Hi II Plants The pBISAM and pBICAB vectors were treated with restriction enzymes Bam HI and Eco RI, and fragments containing SchSAMdc and SchLhca1 nucleotide sequences were obtained with their respective NOS terminators. These fragments were cloned into pTF101.1 vector, in which PTS514 promoter was previously cloned between Hind III and Bam HI sites, therefore obtaining recombinant vectors named pTFSAM514 and pTFCAB514. Said vectors were used for transforming maize Hi II embryos through particle micro-bombardment. FIG. 5 shows graphs indicating total RNA amount expressed in different transgenic plant lines of maize Hi II transformed with pTFSAM514 or pTFCAB514 vectors, subjected to watering suspension during 0 (control), 5 and 12 days. Expression analysis was performed by qRT-PCR. Bars represent mean value of sequence expression, plus/less standard error with n=3. It is possible to observe that plants have a greater expression of SchSAMdc and SchLhca1 sequences when subjected more days to abiotic stress.

Figure 6:
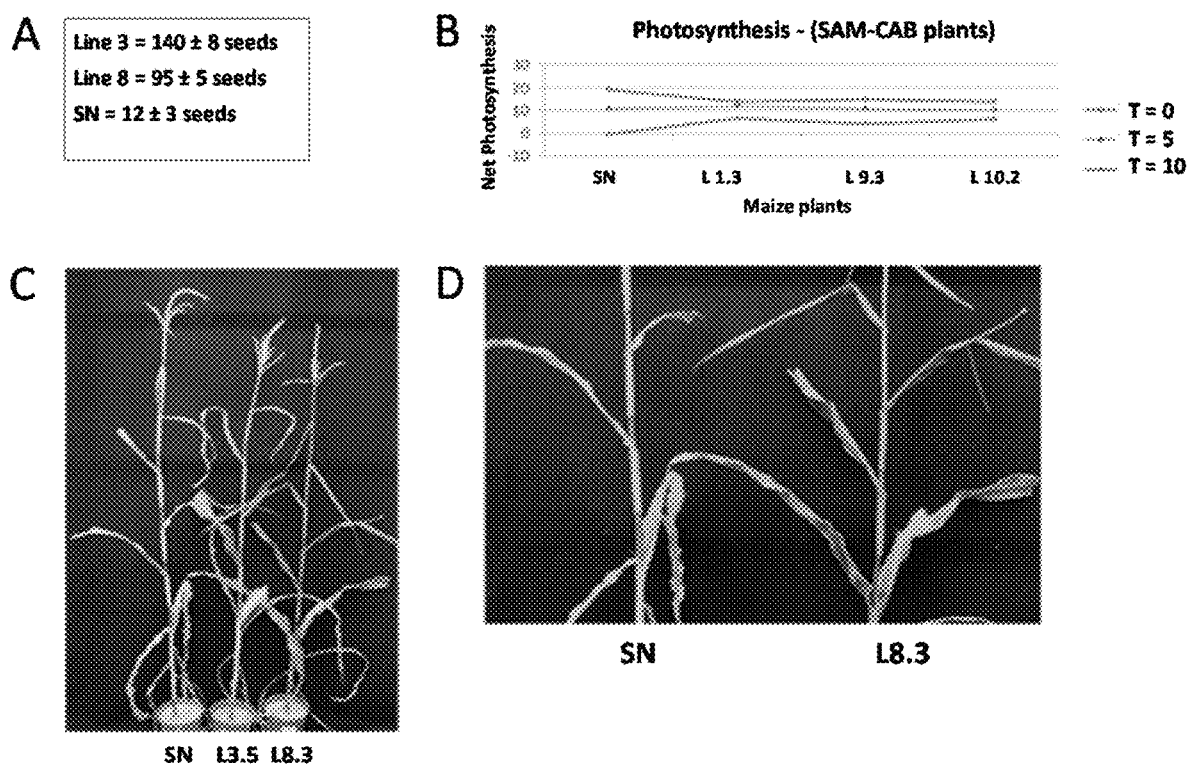
FIG. 6 shows an analysis of Hi ll maize transgenic plants co-transformed with pTFSAM514 and pTFCAB514 vectors and exposed to drought during 15 days under greenhouse culture conditions.

On the other hand, FIG. 6 shows an analysis of transgenic maize Hi II plants co-transformed with pTFSAM514 and pTFCAB514 vectors, exposed to drought for 15 days under greenhouse conditions. Panel A shows the number of seeds obtained in transgenic plants and in null segregants (that is, absence of transgenes) exposed to drought. Panel B shows a graph of net photosynthesis ($CO_2$ amount per leaf area unit in a determined period of time) measured during the drought stress period at 0 (control), 5 and 10 days in transgenic plants and in null segregants. Panel C shows a picture comparing the senescence status of transgenic plants and null segregants. Panel D shows a zoom of the picture in panel C. It is possible to observe that null segregants present a yellowish color, while transgenic plants maintain its green color. This experiment demonstrates that transgenic plants are capable of growing normally under drought conditions.

Example 6: Synthesis of SACA514 Construct

Synthesis of SACA514 construct, as shown in FIG. 2, was performed in a manner to make the construct contain two nucleotide sequences encoding products of interest adequately spaced, and at the same time allowing the possibility to replace only said sequences or only the promoters, without affecting the rest of the construct. A randomly selected linker sequence of 203 base pairs in length was included to maintain an adequate distance between the first NOS terminator and the second PTS514 promoter. At the same time, to allow the individual replacement of sequences (either nucleotide sequences encoding a product of interest or promoters) without affecting the rest of the construct, nucleotide sequences SchSAMdc and SchLhca1 were modified to delete those sequences recognizable by restriction enzymes, without modifying the implicated codons, so that when using those restriction enzymes there would not be an interference or a truncation in nucleotide sequences encoding products of interest. Modified nucleotide sequences SchSAMdc and SchLhca1 are shown in SEQ ID NO:2 (SAM) y SEQ ID NO:3 (CAB), respectively.

Figure 7:
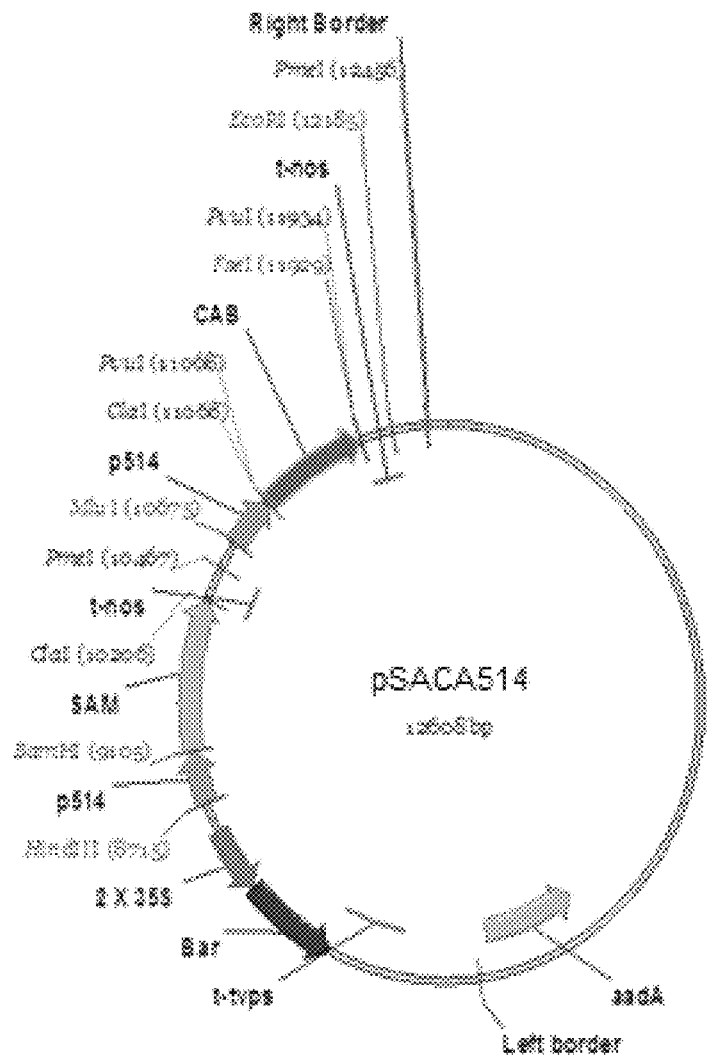
FIG. 7 shows a diagram of the recombinant plasmid denominated pSACA514.

Due to the length of the construct sequence, it was necessary to divide it in parts to synthesize it. Therefore, two fragments were synthesized: the first one of 1967 base pairs in length containing PTS514 promoter, followed by the nucleotide sequence shown in SEQ ID NO:2 (SAM), the NOS terminator and the linker sequence of 203 base pairs in length, flanked by restriction enzyme recognition sequences for Bam HI and Mlu I; and the second fragment containing PTS514 promoter, followed by the nucleotide sequence shown in SEQ ID NO:3 (CAB), 3'UTR from SchLhca1 nucleotide sequence and NOS terminator, flanked by restriction enzyme recognition sequences for Mlu I and Eco RI. Both fragments, once synthesized, were cloned into pUC9 vector, which was amplified in *E. coli* strain DH5-α. Both fragments were released from the vector by using the corresponding restriction enzymes and then were isolated using low melting point agarose gel electrophoresis and the E.Z.N.A.™ Gel Extraction Kit (Omega Biotech, USA). Once purified, these fragments were ligated using T4 DNA ligase (Promega, USA) through the common restriction site Mlu I. Subsequently, the DNA construct generated was sub-cloned in pTF101.1 vector, and its correct position was verified by conventional PCR and restriction mapping. This new recombinant plasmid was named pSACA514 and it is shown in FIG. 7.

Example 7: Stable Transformation of Hi II×B73 Maize Plants and Map of Field Tests The obtaining of maize plants transformed with pSACA514 vector was performed through transformation of maize Hi II (self-pollinated) embryos using *Agrobacterium tumefaciens*. Briefly, the transformation protocol comprised the following steps:

Transformation of *Agrobacterium* with pSACA514 construct;

Transfection of embryos with recombinant *Agrobacterium* having pSACA514 construct;

Cultivation of maize explants in selective media to obtain recombinant calluses;

Regeneration of selected explants to obtain transformed plant lines in conditions controlled in vitro.

Subsequently, from these lines denominated T0, a group was selected and transferred to greenhouse conditions for adapting and growing, and later crossing with pollen from maize B73 pure line. Thus, seeds from 17 T0 lines crossed with B73 lines were obtained, where 50% of the segregant population corresponded to null segregants (absence of transgenes) and the remaining 50% corresponded to hemizygote segregants (single copy of the gene), and then were used in subsequent field tests.

The field test proposed three different water irrigation conditions compared with watering soil to field capacity under an alpha-lattice design (0.1) for 49 genotypes with 3 replicates and a block size of 10. This was performed in this manner, due to SACA514 construct was compared with other 3 genetic construct. The design was used with Gendex software (module ALPHA 6.0), with the parameters previously indicated.

During the test, plants were screened using a group of parameters to determine drought tolerance and performance reached under these conditions. Between the parameters to be considered are: volumetric relative humidity of soil for the different treatments, plants net photosynthesis, green status of the plant (spad values), expression of nucleotide sequences of interest, number of leaves, corn cobs size, dry weight of 100 grains, total grain number per plant, total yield per plant; all of them evaluated in null segregant plants and transgenic plants.

The test was done in Panguilemo Experimental Field of University of Talca (35° 23'S, 71° 40' W, 100 masl—meters above sea level), started on Nov. 28, 2014 where total culture area was 361.05 m² and preparation of the planting bed was made through tillage and soil raking leaving ridges of 20 cm in height. To ensure the existence of null segregant and transgenic plants, seeds were planted in trays containing peat substrate and sterile leaf mould in a 1:1 proportion.

Figure 8:
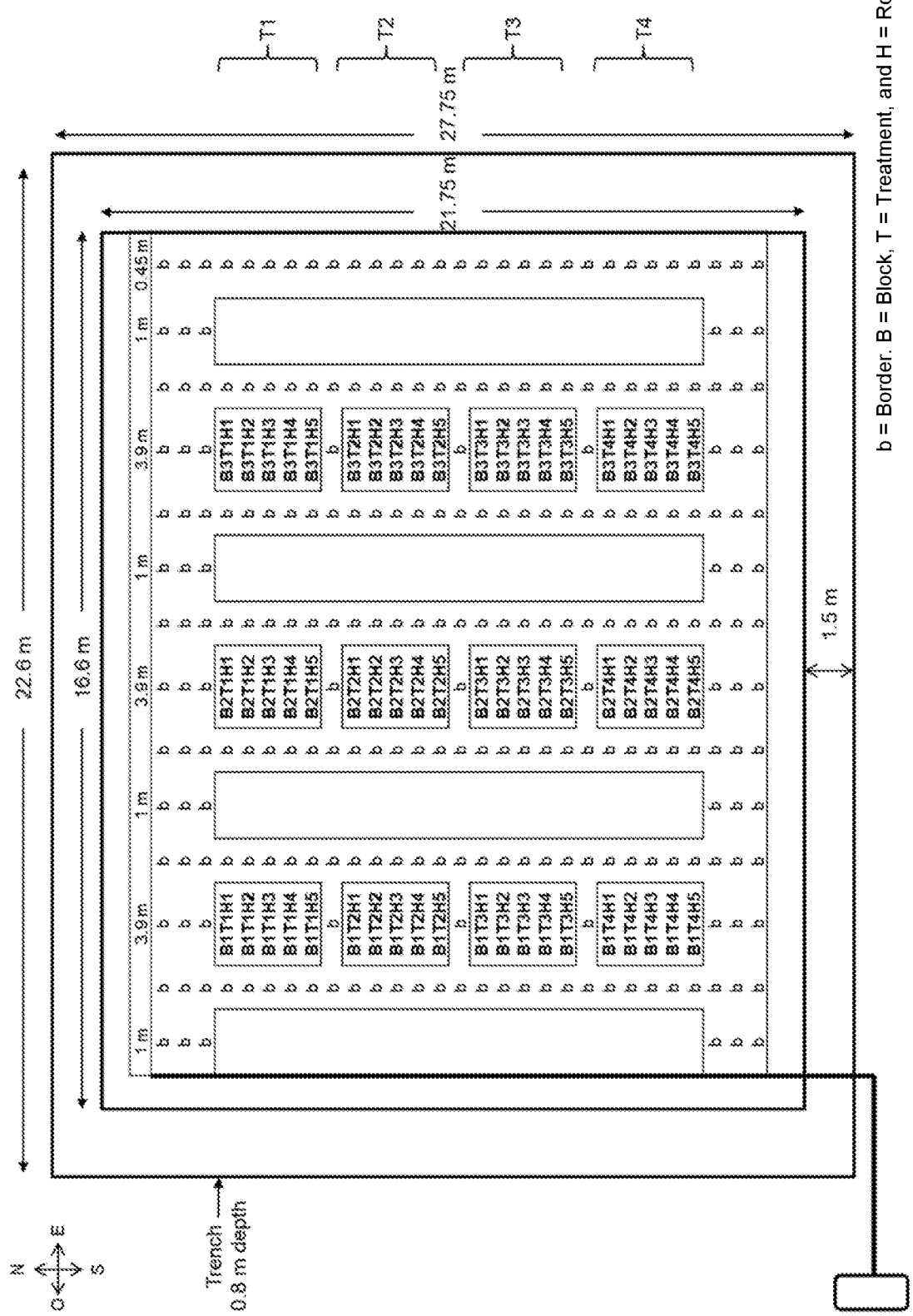
FIG. 8 shows a diagram of the field test design for transgenic Hi II×B73 maize plants and null segregant plants, under different drought treatments.

When seedlings reached the phenological stage of three true leaves their genotype was determined; for this purpose, an extreme of the second true leave was cut (1 cm approximately) and then was tested in a 120 mg/mL solution of glufosinate-ammonium (BASTA). Transgenic plants did not show changes in their green status, however, null segregants showed clear signs of necrosis. Once identified transgenic plants and null segregant plants, all of them were transplanted the same day through a manual system and at a density of 7.3 plants per m², placing transgenic SACA514 plants next to its null segregant. Thus, seeds from 10 of these lines were analyzed. Therefore, there were 100 plants in each block (B1, B2, and B3 in FIG. 8), i.e. 20 plants in each row (H1, H2, H3, H4, and H5 in FIG. 8). FIG. 8 shows the design of the field test.

Example 8: Drought Stress Treatments and Field Test Conditions

Figure 9:
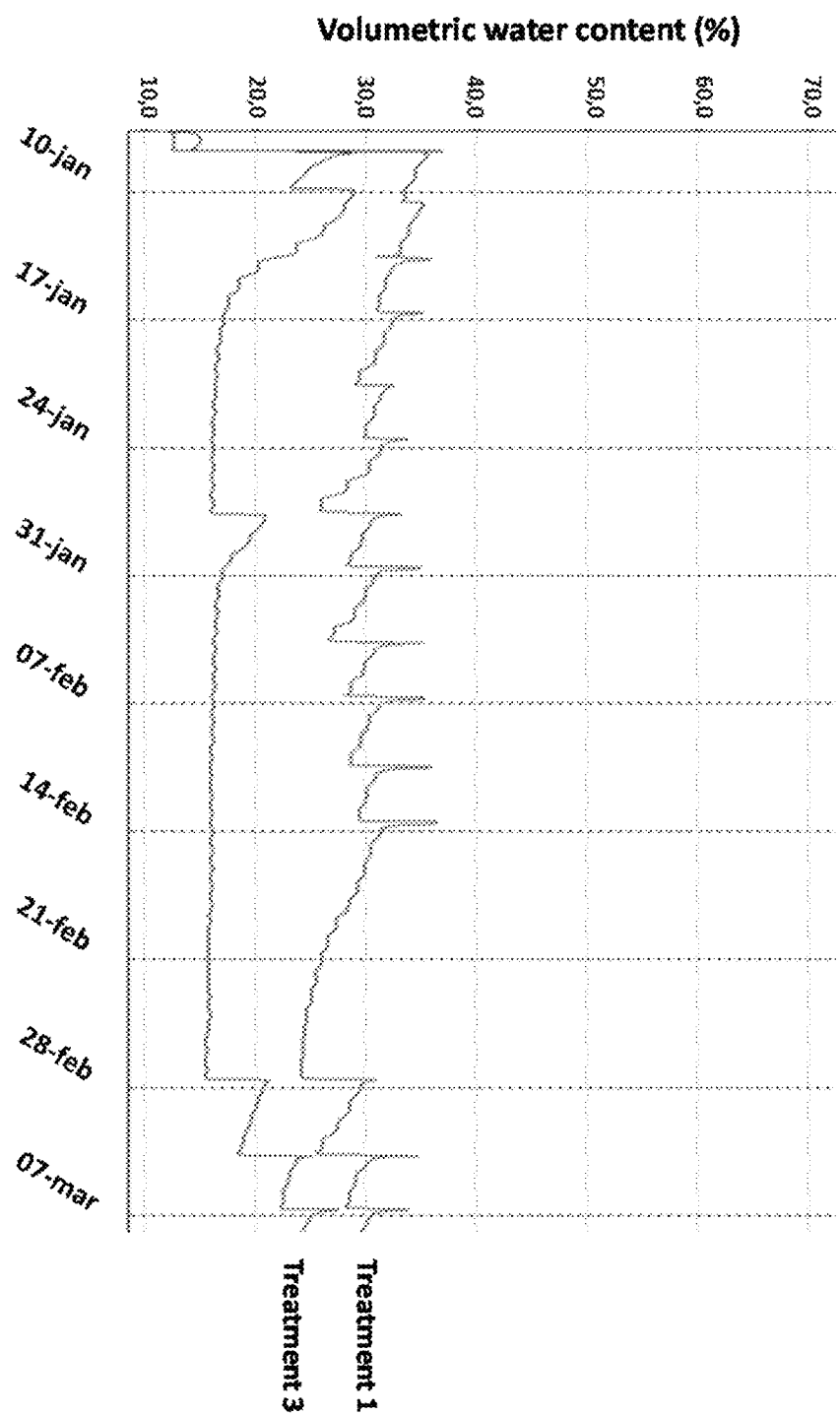
FIG. 9 shows a graph with soil humidity data recorded from treatments with normal watering and in conditions of severe drought.

The test consisted in subjecting plants to drought stress, where three replicates (blocks B1, B2, and B3 in FIG. 8) and four treatments (plots) were used. The first treatment was normal watering (T1 in FIG. 8) and the remaining three consisted in different levels of drought severity (moderate (T2 in FIG. 8), moderately severe (T4 in FIG. 8) and very severe (T3 in FIG. 8)). When plants presented a phenological age corresponding to three weeks before flowering, water irrigation was interrupted to plants of treatment 3 (very severe). On the other hand, for treatment 4 (moderately severe stress) the watering interruption was performed four days later. For treatment 2 (moderate stress), watering interruption was performed the next week. Monitoring of soil humidity was conducted by placing sensors (Decagon) at 40 cm of depth, connected to a data logger through which volumetric water content and soil temperature were determined. These sensors were placed in one of the blocks of each treatment prior to the beginning of the planting process. FIG. 9 shows data registered related to soil humidity. The graph reveals that the lowest soil humidity corresponding to 15% was reached in treatment 3 during anthesis period and grain filling, representing a very low percent in comparison to normal watering treatment corresponding to 25% and restrictive enough, considering the type of soil classified as clay loam (sand 35.3%, silt 28.0%, clay 36.7%) and where the permanent wilting point is obtained with 11% when it is measured between 40 and 70 cm in depth. At a lesser depth, permanent wilting point is around 15%. This point is important since the greatest water absorption of these maize plants is reached between 30 and 40 cm in depth. Moreover, a meteorological station was installed during the test, which enabled the daily determination of precipitation levels, environment temperature, wind speed and leaf humidity. Accumulated data indicated that it was a considerably dry summer, where there were 0.0 mm of precipitation and temperatures fluctuated between 30° C. and 35° C. as maximum and between 17° C. and 20° C. as minimum, with moderated wind and a leaf humidity reaching its maximum at 5:00 AM, increasing towards the end of the test, without being significant to alter the results.

The test proposed that for treatment 2 watering should have been restored in only one opportunity, 10 days after 50% of anthesis (flowering period) and a second irrigation during the grain filling process (grain growing inside the sheath); in treatment 4, watering should have been restored only after grain filling; however, in treatment 3 it should not have been restored during the entire phenological processes of anthesis nor grain filling. Nevertheless, since plants showed clear signs of the effects of stress an emergency watering was needed, which lasted one hour on January, 27th, after plants had completed both phenological stages of anthesis and grain filling. Watering restoring of treatments 3 and 4 were performed the week that followed, while treatment 2 resumed its normal watering four days later. Thus, treatment 3 received only an emergency watering during a total of 52 days.

Figure 10:
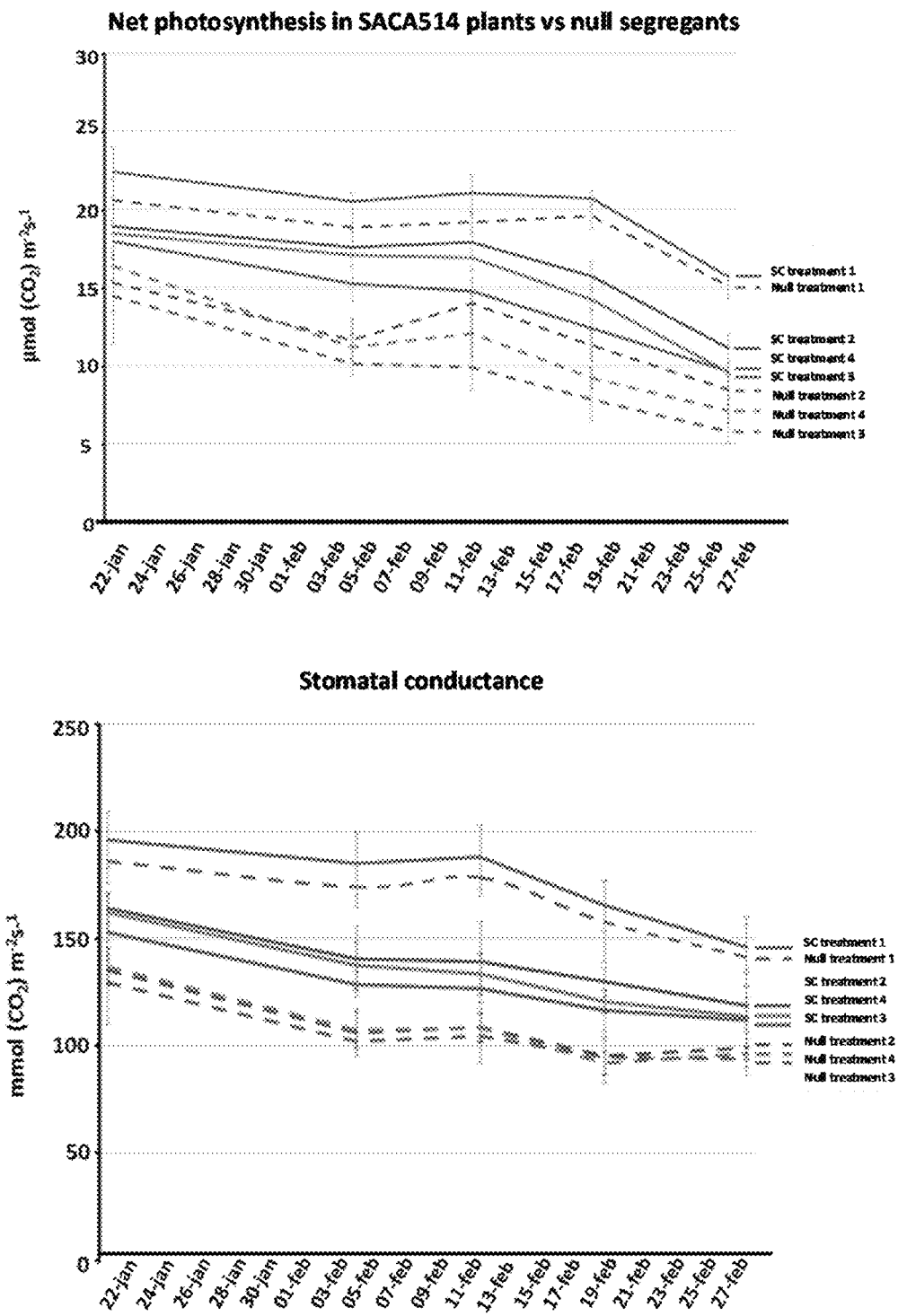
FIG. 10 shows graphs of photosynthesis and stomatal conductance of transgenic Hi II×B73 maize plants containing SACA514 construct in comparison with null segregant plants, under different treatments of drought.

Example 9: Photosynthesis and Stomatal Conductance of SACA514 Transgenic Hi II×B73 Maize Plants Net photosynthesis and stomatal conductance were determined in the leaf located immediately under the node where corn cob arises. Measurements were performed using the portable Photosynthesis Analyzer CIRAS II with a fluorescence module (PP System USA) at 12, 26, 33, 40 and 48 days for each drought treatments mentioned before (considering as time 0 the day of beginning of the test). On the surface of the leaf being studied three measurements were made, and the average value of them was considered as the corresponding value related to the stress period. FIG. 10 shows the results obtained for these tests, where treatment 1 is normal watering, treatment 2 is moderate drought, treatment 3 is very severe drought, treatment 4 is severe drought; SC are transgenic plants containing SACA514 construct, and Null correspond to null segregant plants. It is observed that photosynthesis levels and stomatal conductance exhibited by the different transgenic lines are superior to those shown by null segregant plants. Moreover, this difference is accentuated in the test with the most severe stress treatment (number 3).

Example 10: Relative Water Content and Senescence Status of SACA514 Transgenic Hi II×B73 Maize Plants Relative water content in tissues from leaves of transgenic Hi II×B73 maize plants containing SACA514 construct and their respective null segregants subjected to drought stress and normal watering was determined according to the following formula:

$$RWC = \left(\frac{PF - PS}{PH - PS}\right) \times 100$$

where PF corresponds to leaf dry weight at the moment of collecting the tissue, PH corresponds to leaf dry weight after 24 hours of hydration in distilled water, PS corresponds to dry weight after 8 hours of drying at 80° C. To perform this determination, a 3 cm² piece of leaf was collected from the leaf superior to the node where corn cob arises.

On the other hand, measurements of green status to determine plant senescence status were performed by quantifying the number of leaves maintaining more than 50% of greenness, both in plants containing SACA514 construct and in null segregant plants, until harvest time. FIG. 11 shows graphs regarding relative water content and senescence status (stay-green), where treatment 1 is normal watering, treatment 2 is moderate drought, treatment 3 is very severe drought, treatment 4 is severe drought; SC are transgenic plants containing SACA514 construct, and Null correspond to null segregant plants. Results show that transgenic plants maintain a water content considerably greater than null segregant plants, situation that becomes notably evident in treatment 3. At the same time, these results show that null segregant plants were in a senescence status superior to transgenic plants once finished the biological cycle, but that the senescence status is equaled while the harvest time is being reached. These results were consistent with all the physiological parameters analyzed.

Example 11: Expression Level of Sequences Shown in SEQ ID NO:2 (SAM) and SEQ ID NO:3 (CAB) in SACA514 Transgenic Hi IIxB73 Maize Plants To determine expression levels of nucleotide sequences shown in SEQ ID NO:2 (SAM) and SEQ ID NO:3 (CAB), samples of leaves (100 mg) inserted in the node where corn cob arises were taken at 0, 7, 14, 21 and 28 days after drought stress started. Total RNA was isolated and then purified with SV RNA Total Isolation System kit (Promega), according to the procedure described by suppliers. Purified RNA was treated with DNase I RNase-free (Ambion) to discard DNA contamination. Synthesis of the first chain was performed with First strand cDNA Synthesis kit (Thermo Scientific) according to specifications provided by suppliers. qPCR reactions were performed in a Stratagene MX3000P (Agilent Technologies) thermal cycler using the following parameters:

for nucleotide sequence SEQ ID NO:2 (SAM): 95° C. for 10 minutes, 40 cycles at 95° C. during 15 seconds, 60° C. for 15 seconds, 72° C. for 20 seconds;

for nucleotide sequence SEQ ID NO:3 (CAB): 95° C. for 10 minutes, 40 cycles of 95° C. for 15 seconds, 56° C. for 15 seconds, 72° C. for 20 seconds;

Each reaction contained 10 μL of SYBR Green Master Mix (Stratagene) and 0.25 μM of each specific primer. Additionally, sequences originated from maize encoding Cyclophilin (CYP) (GenBank access code X68678) and Actin1 (ACT) (GenBank access code J01238) were used as controls of constitutive expression.

Primers used in amplification were the following:

| Name | Sequence | |
|---|---|---|
| SchSAMdC-Fwd | 5'-GGAAGGAGGAGGAGGAGTAGC-3' | (SEQ ID NO: 6) |
| SchSAMdC-Rev | 5'-ATTGCCAAATGTTTGAACGATCATC-3' | (SEQ ID NO: 7) |
| SchLhca1-Fwd | 5'-AACAACCTCGTGAAACTCTCC-3' | (SEQ ID NO: 8) |
| SchLhca1-Rev | 5'-ACTTTATTGCCAAATGTTTGAACG-3' | (SEQ ID NO: 9) |
| ZmCYP-Fwd | 5'-GTGTGGATCTGTGAACCCCAT-3' | (SEQ ID NO: 10) |
| ZmCYP-Rev | 5'-CAGGTGAAACACGAATCAAGCA-3' | (SEQ ID NO: 11) |
| ZmACT-Fwd | 5'-GATGGTCAGGTCATCACCATTG-3' | (SEQ ID NO: 12) |
| ZmACT-Rev | 5'-AACAAGGGATGGTTGGAACAAC-3' | (SEQ ID NO: 13) |

The specificity of reaction was verified by melting curve analysis and relative quantification through ΔCt comparative method. FIG. 12 shows the results of expression of sequences SEQ ID NO:2 (SAM, FIG. 12A) and SEQ ID NO:3 (CAB, FIG. 12B), where T1 is treatment with normal watering, T2 is treatment with moderate stress, T3 is treatment with very severe drought and T4 is treatment with severe drought; SAM corresponds to SEQ ID NO:2 (SAM) and CAB corresponds to SEQ ID NO:3 (CAB). Graphs show mean and standard error of five biological replicates and three technical replicates. Results indicate that expression of said sequences was initiated from day 2 of drought in the different treatments, and that expression levels increased until 25 times 14 days after the stress was initiated in comparison with the control (0 days after drought stress initiation); the expression level was maintained until day 21 and then increased until 28 times in day 28 of drought in comparison to control in treatment T3.

Figure 13:
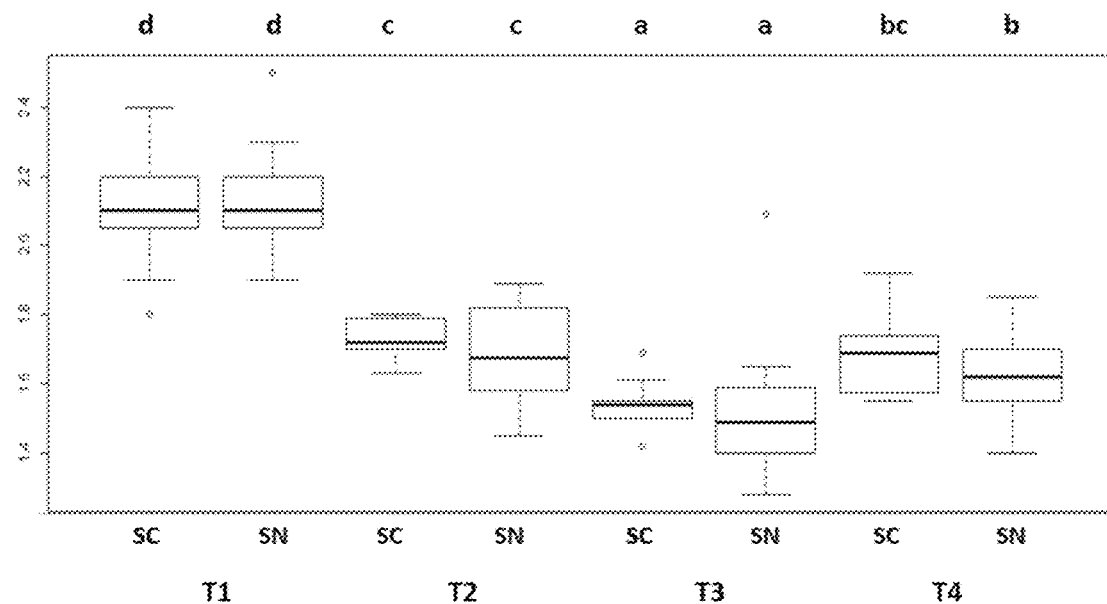
FIG. 13 shows a statistic analysis of the height of transgenic Hi II×B73 maize plants containing SACA514 construct in comparison with null segregant plants, under different drought treatments.
Figure 14:
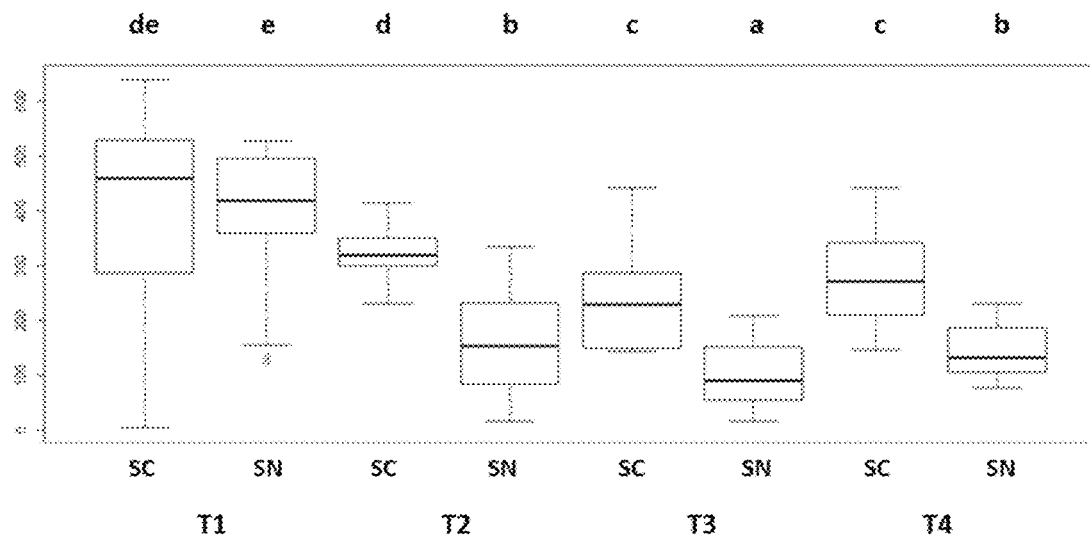
FIG. 14 shows a statistic analysis of the number of maize grains obtained per plant, derived from transgenic Hi II×B73 maize plants containing SACA514 construct in comparison with null segregant plants, under different drought treatments.
Figure 15:
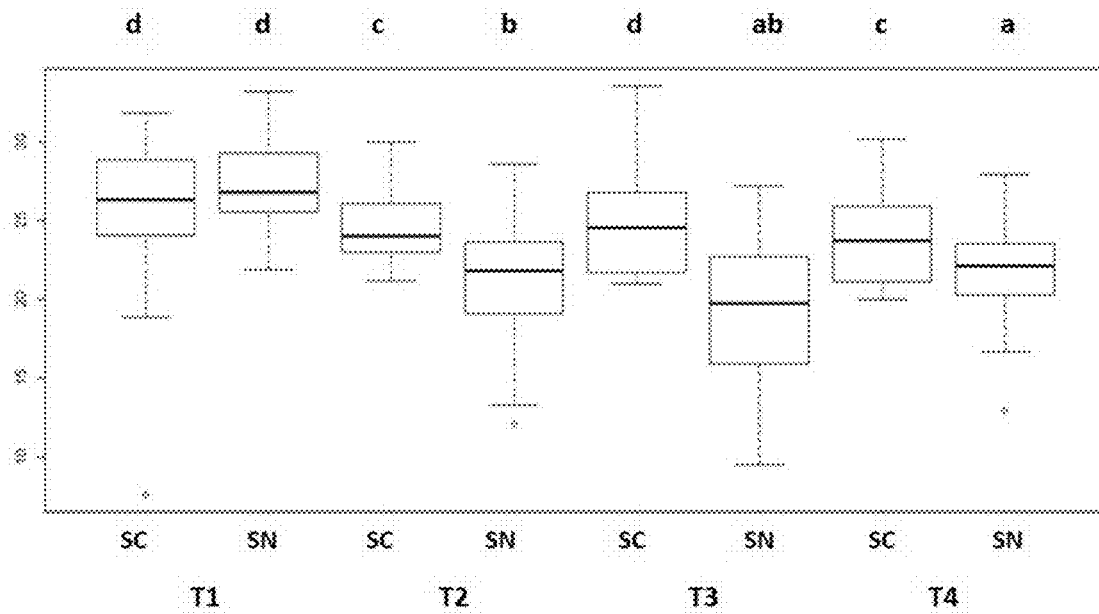
FIG. 15 shows a statistic analysis of dry weight of 100 maize grains, derived from transgenic Hi II×B73 maize plants containing SACA514 construct in comparison with null segregant plants, under different drought treatments.

Example 12: Phenotypic Parameters in SACA514 Transgenic Hi IIxB73 Maize Plants In the moment of harvest (harvesting time), determination of other phenotypic parameters of plants was conducted, such as: height (results shown in FIG. 13), number of maize grains obtained per plant (results shown in FIG. 14) and dry weight of 100 maize grains (results shown in FIG. 15), as well as yield in dry weight in grams per plant (results shown in FIG. 16), which allowed to determine the overall yield per plant and to compare it with results obtained in transgenic plants and null segregant plants.

Figure 16:
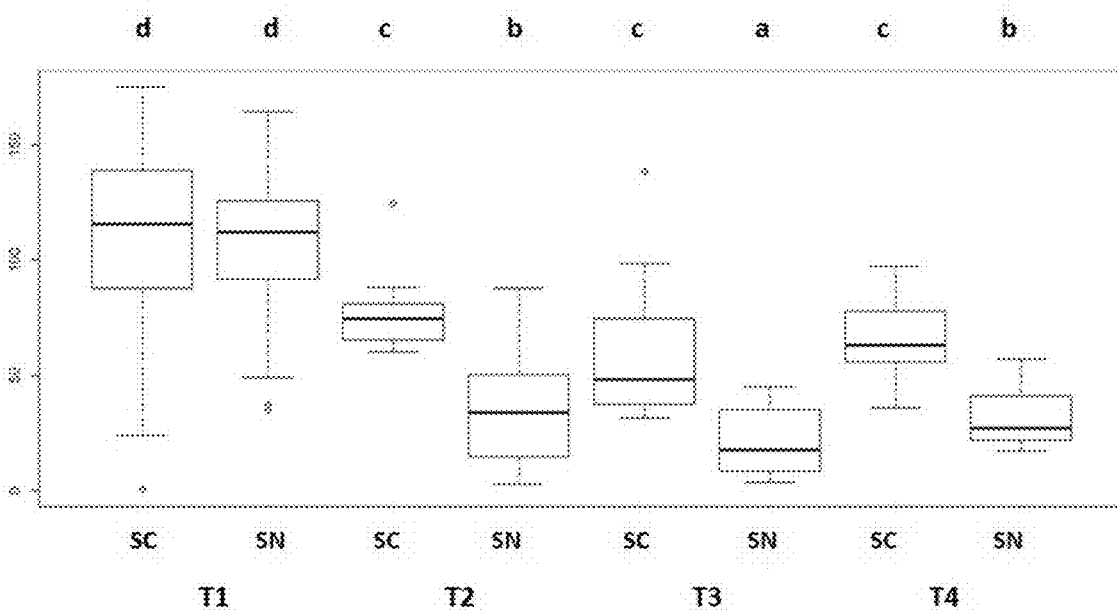
FIG. 16 shows a statistic analysis of dry weight yield in grams per plant, derived from transgenic Hi II×B73 maize plants containing SACA514 construct in comparison with null segregant plants, under different drought treatments.
Figure 17:
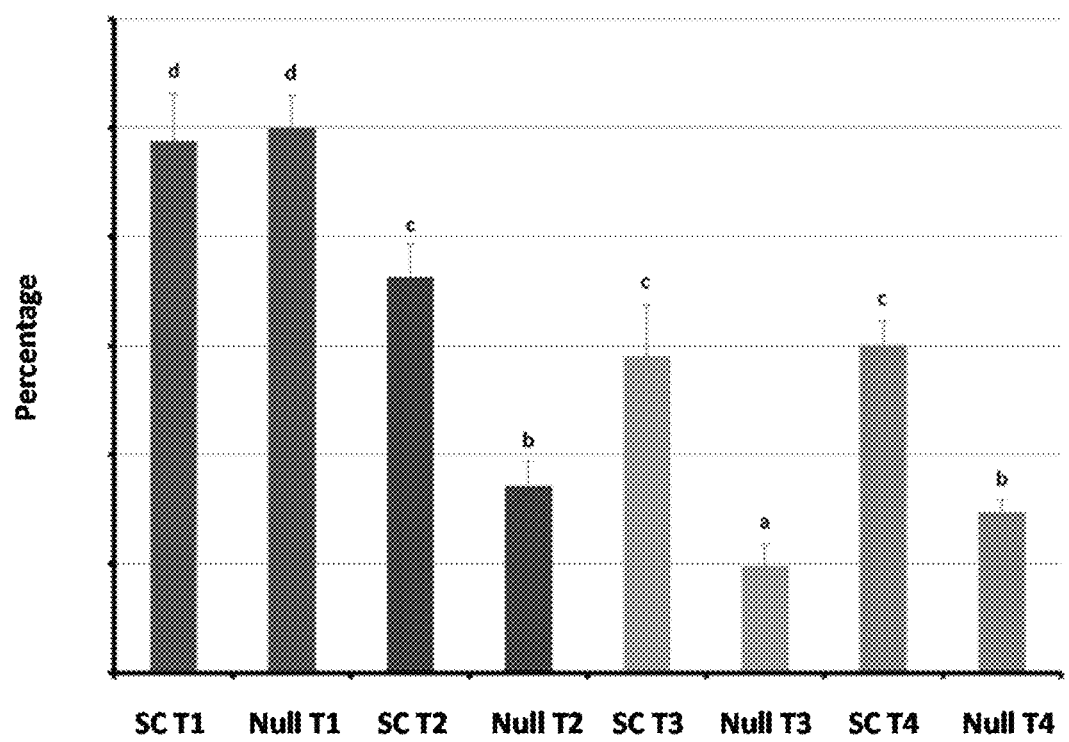
FIG. 17 shows a graph of the percent of dry weight yield in grams per plant, derived from transgenic Hi II×B73 maize plants containing SACA514 construct in comparison with null segregant plants, under different drought treatments.

To compare the yield of plants, statistical analyses were performed with the obtained values in measurements made in plants during harvesting time. Data were analyzed with the statistical computer program R 3.1.0 version (R Core Team 2014). Generalized linear mixed models were utilized were used, specifying the "block" effect as random and the effects "treatment" and "DNA construct" as fixed. Discarding the influence of blocks in these results, average values of groups in the treatments were compared using a contrast Tukey's test. FIGS. 13, 14, 15 and 16 show graphs with statistical results, where T1 is treatment with normal watering, T2 is treatment with moderate drought, T3 is treatment with very severe drought and T4 is treatment with severe drought; SC are transgenic plants containing SACA514 construct, and SN are null segregant plants. Letters a, b, c and d in each graph represent significant statistical difference, considering p<0,05. To a better visualization of results, these are shown in box diagrams. The lower end of the box represents first quartile (value greater than 25% of data), the upper end represents third quartile (value greater than 75% of data), and the central line represents median value. Lines emerging from boxes represent extreme values. It is clearly observed that plants carrying SACA514 construct show a better performance in comparison with null segregant plants, which can be noted in plant height (FIG. 13), the number of grains produced (FIG. 14), dry weight of 100 grains (FIG. 15) and yield per plant (FIG. 16). In FIG. 17 performance data obtained from statistical analysis are represented in a graph considering yield obtained in the control treatment or with a 100% of watering, and are compared with data obtained in each treatment, where T1 is treatment with normal watering, T2 is treatment with moderate drought, T3 is treatment with very severe drought and T4 is treatment with severe drought; SC are transgenic plants containing SACA514 construct, and Null are null segregant plants. Letters a, b, c and d in the graph represent significant statistical difference between average yield (grams of seeds produced per plant) of groups, considering p<0,05. Results obtained are surprising, since null segregant plants subjected to moderate and severe treatments reached a maximum yield of a 30% in relation to irrigated controls, however transgenic plants presented a yield superior to 60%. Additionally, transgenic plants having SACA514 construct in the very severe treatment presented a yield of 60%, while null segregant plants reached only 20% of yield under the same drought conditions. These results show that sequences indicated in SEQ ID NO:2 (SAM) and SEQ ID NO:3 (CAB) were adequately expressed in carrier plants and also are able to increase productivity in an approximately 40% more than plants not having said sequences (null segregants) under the same drought conditions.

On the other hand, FIG. 18 shows pictures of corn cobs obtained in harvesting time from transgenic Hi llxB73 maize plants containing SACA514 construct and null segregant plants for both treatment 1 with continuous watering and treatment 3 of severe drought, where SC are transgenic plants containing SACA514 construct and SN are null segregant plants. It is clearly observed that corn cobs obtained from transgenic plants subjected to severe drought conditions (treatment 3) have a longer length and a greater number of grains than corn cobs obtained from null segregant plants.

In conclusion, transgenic Hi llxB73 maize plants containing SACA514 construct, that is to say, containing the inducible PTS514 promoter and nucleotide sequences shown in SEQ ID NO:2 and SEQ ID NO:3 from the present invention exhibit:
- a rate of carbon fixation or net photosynthesis (FIG. 10) higher than null segregant plants, indicating an efficient water usage and biomass production under stress conditions, probably due to a lesser damage produced to the photosynthetic system;
- a stomatal conductance higher than null segregant plants in all water deficiency treatments (FIG. 10), where it is shown that values obtained from transgenic plants are superior to null segregant plants, making evident that stomatal opening is greater and, therefore, coincident with results obtained in net photosynthesis;
- a reduction of relative water content (RWC) lesser than null segregant plants (FIG. 11), where it is shown that transgenic lines maintain RWC values higher than null segregant plants, which allows them to have a better condition for fertilization and grain filling;
- a chlorophyll loss lesser than null segregant plants (FIG. 11), suggesting a senescence delay in leaves caused by drought;
- a yield regarding to number of grains per plant (FIG. 14) and their dry weight (FIG. 15) higher than null segregant plants, whose percentage ratio indicated that transgenic plants present a higher yield in at least 40% in comparison to null segregant plants (FIGS. 17 and 18);
- a controlled expression of nucleotide sequences shown in SEQ ID NO:2 and SEQ ID NO:3, only when plants are subjected to water deficit conditions (FIGS. 12A and 12B), moreover indicating that expression is consistent with intensity of the stress imposed in each treatment.

With the examples hereby shown, it is clearly evident that PTS514 promoter is capable of regulate induced expression of nucleotide sequences encoding products of interest, suggesting that tolerance to abiotic stress can be extensive to monocotyledonous and dicotyledonous plants with agricultural importance, maintaining high levels of productive yield.

The invention claimed is:

1. A promoter inducible under drought conditions in maize or tomato, comprising
a nucleotide sequence as set forth in SEQ ID NO:1.

2. A DNA construct comprising the promoter of claim 1, operably linked to a DNA sequence encoding a product of interest.

3. The DNA construct of claim 2, wherein the DNA sequence encoding the product of interest is selected from the group consisting of:
   i) a nucleotide sequence encoding an enzyme S-adenosylmethionine decarboxylase;
   ii) a nucleotide sequence encoding a protein 1 chlorophyll a/b binding protein (CAB6) in the light harvesting complex from photosystem I (PSI); and
   c) any combination of sequences defined in a) and b).

4. An expression vector comprising a nucleotide sequence selected from the group consisting of:
   i. a promoter inducible under drought conditions in maize or tomato comprising a nucleotide sequence shown in SEQ ID NO:1; and
   ii. a DNA construct comprising the promoter inducible under drought conditions in maize or tomato comprising the nucleotide sequence as set forth in SEQ ID NO:1, operably linked to a DNA sequence encoding a product of interest.

5. A transformed maize or tomato cell comprising a nucleotide sequence selected from the group consisting of:
   i. a promoter inducible under drought conditions comprising a nucleotide sequence
   as set forth in SEQ ID NO:1;
   ii. a DNA construct comprising a promoter inducible under drought conditions comprising the nucleotide sequence in SEQ ID NO:1, operably linked to a DNA sequence encoding a product of interest;
   and
   iii. the expression vector of claim 4.

6. A transgenic maize or tomato cell comprising, inserted in its genome, a nucleotide sequence selected from the group consisting of:
   i. a promoter inducible under drought conditions comprising a nucleotide sequence as set forth in SEQ ID NO:1
   ii. a DNA construct comprising a promoter inducible under drought conditions comprising the nucleotide sequence
   shown in SEQ ID NO:1, operably linked to a DNA sequence encoding a product of interest; and
   iii. the expression vector of claim 4.

7. A callus of transgenic maize or tomato cells comprising at least one transgenic cell according to claim 6.

8. A transgenic maize or tomato plant comprising at least one transgenic cell according to claim 6.

9. A method for expressing a nucleotide sequence encoding a product of interest in a maize or tomato plant under drought conditions comprising the steps of transforming a cell of any of said plants with the expression vector of claim 4, obtaining from said cell a callus of transgenic cells, and regenerating a plant from said callus.

10. The DNA construct of claim 3, wherein the nucleotide sequence encoding the enzyme S-adenosylmethionine decarboxylase is the nucleotide sequence as set forth in SEQ ID NO:2; and the nucleotide sequence encoding the protein 1 chlorophyll a/b binding protein (CAB6) in the light harvesting complex from photosystem I (PSI) is the nucleotide sequence as set forth in SEQ ID NO:3.

11. The DNA construct of claim 10, further comprising a linker sequence operably linked to the nucleotide sequence as set forth in SEQ ID NO:2, and the promoter operably linked to the nucleotide sequence as set forth in SEQ ID NO:3.

12. The DNA construct of claim 11, wherein said linker sequence is a random sequence between 120 and 400 base pairs in length.

13. The expression vector of claim 4, wherein the DNA sequence encoding the product of interest is selected from the group consisting of:
   a) a nucleotide sequence encoding an enzyme S-adenosylmethionine decarboxylase;
   b) a nucleotide sequence encoding a protein 1 chlorophyll a/b binding protein (CAB6) in the light harvesting complex from photosystem I (PSI); and
   c) any combination of sequences defined in a) and b).

14. The expression vector of claim 13, wherein the nucleotide sequence encoding the enzyme S-adenosylmethionine decarboxylase is the nucleotide sequence as set forth in SEQ ID NO:2; and the nucleotide sequence encoding the protein 1 chlorophyll a/b binding protein (CAB6) in the light harvesting complex from photosystem I (PSI) is the nucleotide sequence as set forth in SEQ ID NO:3.

15. The expression vector of claim 14, further comprising a linker sequence operably linked to the nucleotide sequence as set forth in SEQ ID NO:2, and the promoter operably linked to the nucleotide sequence as set forth in SEQ ID NO:3.

16. The expression vector of claim 15, wherein said linker sequence is a random sequence between 120 and 400 base pairs in length.

* * * * *

UNITED STATES PATENT AND TRADEMARK OFFICE
CERTIFICATE OF CORRECTION

PATENT NO. : 10,851,382 B2
APPLICATION NO. : 15/769527
DATED : December 1, 2020
INVENTOR(S) : Simón Aurelio Ruiz Lara et al.

Page 1 of 1

It is certified that error appears in the above-identified patent and that said Letters Patent is hereby corrected as shown below:

On the Title Page

Item (72)

1st inventor's name is misspelled and should be Simón Aurelio Ruiz Lara

4th inventor's name is misspelled and should be Mónica Loreto Yañez Chávez

Item (73)

2nd Assignees name is misspelled and should be INVERSIONES Y ASESORÍA OLIVARES Y MELOSSI LTDA.

Signed and Sealed this
Eleventh Day of May, 2021

Drew Hirshfeld
*Performing the Functions and Duties of the
Under Secretary of Commerce for Intellectual Property and
Director of the United States Patent and Trademark Office*

SEQUENCE LISTING

```
<160> NUMBER OF SEQ ID NOS: 13

<210> SEQ ID NO 1
<211> LENGTH: 384
<212> TYPE: DNA
<213> ORGANISM: Artificial Sequence
<220> FEATURE:
<223> OTHER INFORMATION: Synthetic promoter

<400> SEQUENCE: 1
tgaggagtcc atccgcgaga accaaacttt gaataacttt gtgccactgc agaagtttgg        60
tagagttggt aatctatgaa gaagaaaaat ttgttttgtg ccatctagaa ggtttggtag       120
agtaggtgag ctatgaagaa gaaaaaattg ttttgtgcca ctgcagaagt ttggtagagt       180
```

| | |
|---|---|
| tggtaatcta tgaagaagaa aaatttgttt tgtgccatct agaaggtttg gtagagtagg | 240 |
| tgagctatga agaagaaaaa attgtttttc ttctatagca catttggagg gtagtgtatt | 300 |
| tgttctctat aaaagggagg acaattcttc attctaagta caccaaaaag aattacaaag | 360 |
| gagagaaaaa aagagtgagg catc | 384 |

<210> SEQ ID NO 2
<211> LENGTH: 1077
<212> TYPE: DNA
<213> ORGANISM: Artificial Sequence
<220> FEATURE:
<223> OTHER INFORMATION: Primer

<400> SEQUENCE: 2

| | |
|---|---|
| atggacttgc cggtgtccgc catcggcttc gacggcttcg acaagagact cgacatctcc | 60 |
| ttcgtcgagc cgggcctgtt cgccgacccg aacggcaagg gcctccgctc cctcaccaag | 120 |
| gcccagttgg acgagatcct cggcccggcc gagtgcacca tcgtggacaa cctgtccaac | 180 |
| gactacgtgg actcctacgt gctgtccgag tccagcctct tcgtgtactc ctacaagatc | 240 |
| atcatcaaga cctgcggcac caccaagctg ctcctcgcca tcccgccgat cctgagattg | 300 |
| gccgagacct tgtccctcaa ggtgcaagac gtgagataca cccgcggcag cttcatcttc | 360 |
| ccgggcgccc aatccttccc gcaccgccac ttctccgacg acgtggccgt cctcgacggc | 420 |
| tacttcggca agctcgccgc cggcagcaag gccgtgatca tgggcaaccc ggacaagacc | 480 |
| cagaagtggc acgtgtactc cgcctccgcc ggcaccgtgc agtgcaacga cccggtgtac | 540 |
| accctcgaga tgtgcatggc cggcttggac agagagaagg cctccgtctt ctacaagacc | 600 |
| gacgacagct ccgccgccca catgaccgtg agatccggca tcagaaagat cctcccgaag | 660 |
| ttcgagatct gcgacttcga gttcgacccg tgcggctact ccatgaactc catcgacggc | 720 |
| gccgccgtgt ccaccatcca catcaccccg gaggacggct tcagctacgc cagcttcgac | 780 |
| tccgtgggct acgacccgaa gaccaccgag ttgggcccgc tggtggagag agtgctcgcc | 840 |
| tgcttcgagc cggccgagtt ctccatcgcc ctgcacgccg acgtggccac caagttactg | 900 |
| gagcgcgtgt gctccgtgga cgtgaagggc tactccctcg ccgagtggag cccggacgag | 960 |
| ttcggcaagg gcggctccat cgtctaccag aagttcacca gaaccccgta ctgcgactcc | 1020 |
| ccgaagtccg tcctgaaggg ctgctggaag gaggaggaga aggaggagaa ggagtag | 1077 |

<210> SEQ ID NO 3
<211> LENGTH: 741
<212> TYPE: DNA
<213> ORGANISM: Artificial Sequence
<220> FEATURE:
<223> OTHER INFORMATION: Primer

<400> SEQUENCE: 3

| | |
|---|---|
| atggcctcca acaccttgat gagttgcggc atcccggccg tctgcccgtc cttcctctcc | 60 |
| tccaccaagt ccaaattcgc cgccgcgatg ccggtctacg tcggcgccac caacttcatg | 120 |
| tccagattct ccatgtccgc cgactggatg ccgggccagc cgcgcccgtc ttacctcgac | 180 |
| ggctccgccc cgggcgactt cggcttcgac tccctcggct tggcgaggt gccggccaac | 240 |
| ttggagagat acaaagagtc cgagctcatc cactgcagat gggccatgct cgccgtcccc | 300 |
| ggcatcatcg tgcccgaggc cttgggcttg gcaactgggt caaggcccca agagtgggcc | 360 |
| gccatcccgg gcggccaagc cacctacttg gccagcccg tccgtgggg cacctcccg | 420 |
| accatcttgg ccatcgagtt cttggccatc gccttcgtgg agcaccaaag aagtatggag | 480 |

```
aaagactccg agaagaagaa gtacccgggc ggcgccttcg acccgttggg ctactccaaa      540
gacccggcca aattcgagga gctcaaagtc aaggagatca agaacggtcg cctcgccttg      600
ttggccatcg tgggcttctg cgtgcaacaa tccgcctacc tgggcaccgg cccgttggag      660
aacttggcca cccacttggc cgacccgtgg cacaacaaca tcggcgacgt gatcatcccg      720
aaaggcatct tcccgaacta a                                                741
```

<210> SEQ ID NO 4
<211> LENGTH: 3477
<212> TYPE: DNA
<213> ORGANISM: Artificial Sequence
<220> FEATURE:
<223> OTHER INFORMATION: Synthetic construction

<400> SEQUENCE: 4

```
aagctttgag gagtccatcc gcgagaacca aactttgaat aactttgtgc cactgcagaa       60
gtttggtaga gttggtaatc tatgaagaag aaaaatttgt tttgtgccat ctagaaggtt      120
tggtagagta ggtgagctat gaagaagaaa aattgtttt gtgccactgc agaagtttgg      180
tagagttggt aatctatgaa gaagaaaaat ttgttttgtg ccatctagaa ggtttggtag      240
agtaggtgag ctatgaagaa gaaaaaattg ttttt cttct atagcacatt tggagggtag      300
tgtatttgtt ctctataaaa gggaggacaa ttcttcattc taagtacacc aaaaagaatt      360
acaaaggaga gaaaaaaaga gtgaggcatc ggatccatgg acttgccggt gtccgccatc      420
ggcttcgacg gcttcgacaa gagactcgac atctccttcg tcgagccggg cctgttcgcc      480
gacccgaacg gcaagggcct ccgctccctc accaaggccc agttggacga gatcctcggc      540
ccggccgagt gcaccatcgt ggacaacctg tccaacgact acgtggactc ctacgtgctg      600
tccgagtcca gcctcttcgt gtactcctac aagatcatca tcaagacctg cggcaccacc      660
aagctgctcc tcgccatccc gccgatcctg agattggccg agaccttgtc cctcaaggtg      720
caagacgtga gatacacccg cggcagcttc atcttcccgg gcgcccaatc cttcccgcac      780
cgccacttct ccgacgacgt ggccgtcctc gacggctact cggcaagct cgccgccggc      840 agcaaggccg tgatcatggg caacccggac aagacccaga gtggcacgt gtactccgcc      900 tccgccggca ccgtgcagtg caacgacccg gtgtacaccc tcgagatgtg catggccggc      960
ttggacagag agaaggcctc cgtcttctac aagaccgacg cagctccgc cgcccacatg     1020 accgtgagat ccggcatcag aaagatcctc ccgaagttcg agatctgcga cttcgagttc     1080
gacccgtgcg gctactccat gaactccatc gacggcgccg ccgtgtccac catccacatc     1140
accccggagg acggcttcag ctacgccagc ttcgactccg tgggctacga cccgaagacc     1200
accgagttgg gccgctggt ggagagagtg ctcgcctgct cgagccggc cgagttctcc     1260 atcgccctgc acgccgacgt ggccaccaag ttactggagc gcgtgtgctc cgtggacgtg     1320
aagggctact ccctcgccga gtggagcccg gacgagttcg gcaagggcgg ctccatcgtc     1380
taccagaagt tcaccagaac cccgtactgc gactccccga gtccgtcct gaagggctgc     1440 tggaaggagg aggagaagga ggagaaggag tagcaccacc accaccacca ccatatggat     1500
cgttcaaaca tttggcaata agtttcttta agattgaatc ctgttgccgg tcttgcgatg     1560
attatcatat aatttctgtt gaattacgtt aagcatgtaa taattaacat gtaatgcatg     1620
acgttattta tgagatgggt ttttatgatt agagtcccgc aattatacat ttaatacgcg     1680
atagaaaaca aaatatagcg cgcaaactag gataaattat cgcgcgcggt gtcatctatg     1740
```

```
ttactagatc gtttaaacgg gcctcctgtc aatgctggcg gcggctctgg tggtggttct    1800
ggtggcggct ctgagggtgg tggctctgag ggtggcggtt ctgagggtgg cggctctgag    1860
ggaggcggtt ccggtggtgg ctctggttcc ggtgattttg attatgaaaa gatggcaaac    1920
gctaataagg gggctatgac cgaaaatgcc gatgaaaacg cacgcgttga ggagtccatc    1980
cgcgagaacc aaactttgaa taactttgtg ccactgcaga gtttggtag agttggtaat     2040 ctatgaagaa gaaaaatttg ttttgtgcca tctagaaggt ttggtagagt aggtgagcta    2100
tgaagaagaa aaaattgttt tgtgccactg cagaagtttg gtagagttgg taatctatga    2160
agaagaaaaa tttgttttgt gccatctaga aggtttggta gagtaggtga gctatgaaga    2220
agaaaaaatt gttttttcttc tatagcacat ttggagggta gtgtatttgt tctctataaa    2280
agggaggaca attcttcatt ctaagtacac caaaaagaat tacaaaggag agaaaaaaag    2340
agtgaggcat ccgatcgatg gcctccaaca ccttgatgag ttgcggcatc ccggccgtct    2400
gcccgtcctt cctctcctcc accaagtcca aattcgccgc cgcgatgccg gtctacgtcg    2460
gcgccaccaa cttcatgtcc agattctcca tgtccgccga ctggatgccg gccagccgc    2520 gcccgtctta cctcgacggc tccgccccgg gcgacttcgg cttcgactcc ctcggcttgg    2580
gcgaggtgcc ggccaacttg gagagataca agagtccga gctcatccac tgcagatggg     2640
ccatgctcgc cgtccccggc atcatcgtgc ccgaggcctt gggcttgggc aactgggtca    2700
aggcccaaga gtgggccgcc atcccgggcg gccaagccac ctactgggc cagcccgtcc     2760 cgtggggcac cctcccgacc atcttggcca tcgagttctt ggccatcgcc ttcgtggagc    2820
accaaagaag tatggagaaa gactccgaga agaagaagta cccgggcggc gccttcgacc    2880
cgttgggcta ctccaaagac ccggccaaat tcgaggagct caaagtcaag gagatcaaga    2940
acggtcgcct cgccttgttg gccatcgtgg gcttctgcgt gcaacaatcc gcctacctgg    3000
gcaccggccc gttggagaac ttggccaccc acttggccga cccgtggcac aacaacatcg    3060
gcgacgtgat catcccgaaa ggcatcttcc cgaactaaat cgtgctgttc atcatctagt    3120
acatcagcca aaaacacctc gtgaaactct cccacgtgct gatcgacttc taatggaacg    3180
gcctcttcgt gtcaccacca ccaccaccac ggccggccga tcgttcaaac atttggcaat    3240
aaagtttctt aagattgaat cctgttgccg gtcttgcgat gattatcata taatttctgt    3300
tgaattacgt taagcatgta ataattaaca tgtaatgcat gacgttattt atgagatggg    3360 ttttttatgat tagagtcccg caattataca tttaatacgc gatagaaaac aaaatatagc    3420
gcgcaaacta ggataaatta tcgcgcgcgg tgtcatctat gttactagat cgaattc       3477
```

```
<210> SEQ ID NO 5
<211> LENGTH: 203
<212> TYPE: DNA
<213> ORGANISM: Artificial Sequence
<220> FEATURE:
<223> OTHER INFORMATION: Random nucleotides

<400> SEQUENCE: 5
gggcctcctg tcaatgctgg cggcggctct ggtggtggtt ctggtggcgg ctctgagggt     60
ggtggctctg agggtggcgg ttctgagggt ggcggctctg agggaggcgg ttccggtggt    120
ggctctggtt ccggtgattt tgattatgaa aagatggcaa acgctaataa gggggctatg    180
accgaaaatg ccgatgaaaa cgc                                           203

<210> SEQ ID NO 6
<211> LENGTH: 21
```

```
<212> TYPE: DNA
<213> ORGANISM: Artificial Sequence
<220> FEATURE:
<223> OTHER INFORMATION: Primer

<400> SEQUENCE: 6
ggaaggagga ggaggagtag c                                              21

<210> SEQ ID NO 7
<211> LENGTH: 25
<212> TYPE: DNA
<213> ORGANISM: Artificial Sequence
<220> FEATURE:
<223> OTHER INFORMATION: Primer

<400> SEQUENCE: 7
attgccaaat gtttgaacga tcatc                                          25

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
aacaacctcg tgaaactctc c                                              21

<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9
actttattgc caaatgtttg aacg                                           24

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
gtgtggatct gtgaacccca t                                              21

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
caggtgaaac acgaatcaag ca                                             22

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
```

-continued

```
gatggtcagg tcatcaccat tg                                              22

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
aacaagggat ggttggaaca ac                                              22
```